(12) United States Patent
Everett et al.

(10) Patent No.: US 9,778,131 B2
(45) Date of Patent: Oct. 3, 2017

(54) PRESSURE DATA ACQUISITION ASSEMBLY

(71) Applicant: ORPYX MEDICAL TECHNOLOGIES INC., Calgary (CA)

(72) Inventors: Julia Breanne Everett, Calgary (CA); Marcel Groenland, Calgary (CA); Amanda Rae Hehr, Calgary (CA); Daryl David Coutts, Calgary (CA); Llewellyn Lloyd Turnquist, Calgary (CA); Travis Michael Stevens, Calgary (CA)

(73) Assignee: ORPYX MEDICAL TECHNOLOGIES INC., Calgary (CA)

( * ) Notice: Subject to any disclaimer, the term of this patent is extended or adjusted under 35 U.S.C. 154(b) by 517 days.

(21) Appl. No.: 14/283,921

(22) Filed: May 21, 2014

(65) Prior Publication Data
US 2014/0350882 A1  Nov. 27, 2014

Related U.S. Application Data

(60) Provisional application No. 61/825,871, filed on May 21, 2013.

(51) Int. Cl.
*G01L 25/00* (2006.01)
*A61B 5/00* (2006.01)
(Continued)

(52) U.S. Cl.
CPC ............ *G01L 25/00* (2013.01); *A61B 5/1038* (2013.01); *A61B 5/445* (2013.01); *A61B 5/6807* (2013.01);
(Continued)

(58) Field of Classification Search
CPC .... A61B 2562/0223; A61B 2562/0247; A61B 2562/046; A61B 5/445; A61B 5/6833;
(Continued)

(56) References Cited

U.S. PATENT DOCUMENTS 3,791,375 A     2/1974  Pfeiffer
4,251,302 A *   2/1981  Leonard ................... G02C 5/00
                                                           156/329
(Continued)

FOREIGN PATENT DOCUMENTS

CA     2306967 A1    4/1999
CA     2352768 A1    6/1999
(Continued)

OTHER PUBLICATIONS

U.S. Office Action mailed Oct. 11, 2012 in co-pending U.S. Appl. No. 13/284,592.
(Continued)

*Primary Examiner* — John H Le
(74) *Attorney, Agent, or Firm* — Oblon, McClelland, Maier & Neustadt, L.L.P.

(57) ABSTRACT

A method and assembly for acquiring pressure data. A pressure sensor is applied to a target surface on an individual. A calibrator and a processing element are in communication with the pressure sensor. Processing element receives pressure data and provides an integrated pressure value over a measurement time period. The integrated pressure value is compared to an alert value and to a change condition value. Where an alert value is exceeded, an alert is transmitted to an output device for display. Where a change condition value is exceeded, a measurement parameter of the pressure sensor is changed, or the calibrator is applied to the pressure sensor to recalibrate the pressure sensor to a recalibrated pressure range.

18 Claims, 13 Drawing Sheets

(51) Int. Cl.
  *G01D 3/08* (2006.01)
  *A61B 5/103* (2006.01)
  *A61G 7/057* (2006.01)
  *G01L 19/12* (2006.01)
  *G01L 27/00* (2006.01)

(52) U.S. Cl.
  CPC ............. *A61B 5/6833* (2013.01); *G01D 3/08* (2013.01); *A61B 5/7225* (2013.01); *A61B 5/746* (2013.01); *A61B 2562/0223* (2013.01); *A61B 2562/0247* (2013.01); *A61B 2562/046* (2013.01); *A61G 7/057* (2013.01); *G01L 19/12* (2013.01); *G01L 27/002* (2013.01)

(58) Field of Classification Search
  CPC ...... A61B 5/7225; A61B 5/746; A61G 7/057; G01D 3/08; G01L 19/12; G01L 25/00; G01L 27/002
  USPC ................ 702/44, 47, 85, 98, 104; 156/329; 600/587, 595
  See application file for complete search history.

(56) References Cited

U.S. PATENT DOCUMENTS

| | | | |
|---|---|---|---|
| 4,554,930 A | 11/1985 | Kress | |
| 4,647,918 A | 3/1987 | Goforth | |
| 5,010,772 A | 4/1991 | Bourland et al. | |
| 5,033,291 A | 7/1991 | Podoloff et al. | |
| 5,054,323 A | 10/1991 | Hubbard, Jr. et al. | |
| 5,505,072 A | 4/1996 | Oreper | |
| 5,642,096 A | 6/1997 | Leyerer et al. | |
| 5,678,448 A | 10/1997 | Fullen et al. | |
| 5,678,566 A | 10/1997 | Dribbon | |
| 5,689,455 A | 11/1997 | Mullarkey et al. | |
| 5,756,904 A | 5/1998 | Oreper et al. | |
| 5,879,292 A | 3/1999 | Sternberg et al. | |
| 5,905,209 A | 5/1999 | Oreper | |
| 6,025,725 A | 2/2000 | Gershenfeld et al. | |
| 6,030,351 A | 2/2000 | Schmidt et al. | |
| 6,055,173 A | 4/2000 | Mullarkey et al. | |
| 6,130,834 A | 10/2000 | Mullarkey et al. | |
| 6,155,120 A | 12/2000 | Taylor | |
| 6,272,936 B1 | 8/2001 | Oreper et al. | |
| 6,273,863 B1 | 8/2001 | Avni et al. | |
| 6,287,253 B1 | 9/2001 | Ortega et al. | |
| 6,360,597 B1 | 3/2002 | Hubbard, Jr. | |
| 6,445,605 B1 | 9/2002 | Mullarkey et al. | |
| 6,661,693 B2 | 12/2003 | Mullarkey et al. | |
| 6,694,826 B2 | 2/2004 | Kiribayashi et al. | |
| 6,712,084 B2 | 3/2004 | Shajii et al. | |
| 6,807,869 B2 | 10/2004 | Farringdon et al. | |
| 6,810,308 B2 | 10/2004 | Shajii et al. | |
| 6,826,071 B2 | 11/2004 | Mullarkey et al. | |
| 6,829,942 B2 | 12/2004 | Yanai et al. | |
| 6,868,862 B2 | 3/2005 | Shajii et al. | |
| 6,903,991 B2 | 6/2005 | Mullarkey et al. | |
| 6,932,098 B2 | 8/2005 | Shajii et al. | |
| 6,948,508 B2 | 9/2005 | Shajii et al. | |
| 6,963,772 B2 | 11/2005 | Bloom et al. | |
| 7,004,191 B2 | 2/2006 | Shajii et al. | |
| 7,030,764 B2 | 4/2006 | Smith et al. | |
| 7,136,767 B2 | 11/2006 | Shajii et al. | |
| 7,260,999 B2 | 8/2007 | Divigalpitiya et al. | |
| 7,424,346 B2 | 9/2008 | Shajii et al. | |
| 7,535,108 B2 | 5/2009 | Saimen | |
| 7,552,015 B2 | 6/2009 | Shajii et al. | |
| 7,587,937 B2 | 9/2009 | Haselhurst et al. | |
| 7,597,676 B2 | 10/2009 | Dunn et al. | |
| 7,625,117 B2 | 12/2009 | Haslett et al. | |
| 7,687,678 B2 | 3/2010 | Jacobs | |
| 7,716,005 B2 | 5/2010 | Shoureshi et al. | |
| 7,726,206 B2 | 6/2010 | Terrafranca, Jr. et al. | |
| 7,809,473 B2 | 10/2010 | Shajii et al. | |
| 7,869,164 B2 | 1/2011 | Shin | |
| 8,011,041 B2 | 9/2011 | Hann | |
| 8,111,165 B2 | 2/2012 | Ortega et al. | |
| 8,121,800 B2 | 2/2012 | Altman et al. | |
| 8,150,553 B2 | 4/2012 | Shajii et al. | |
| 8,285,356 B2 | 10/2012 | Bly et al. | |
| 8,308,714 B2 | 11/2012 | Weston et al. | |
| 8,454,539 B2 | 6/2013 | Vuillerme et al. | |
| 8,535,246 B2 | 9/2013 | Drennan et al. | |
| 8,738,187 B2 | 5/2014 | Shajii et al. | |
| 8,925,392 B2 | 1/2015 | Esposito et al. | |
| 8,994,528 B2 | 3/2015 | Celik-Butler et al. | |
| 9,074,954 B2 | 7/2015 | Tseng et al. | |
| 9,188,963 B2 | 11/2015 | Gray et al. | |
| 9,204,797 B2 | 12/2015 | Gray et al. | |
| 9,356,003 B1 | 5/2016 | Zhou | |
| 9,451,881 B2 | 9/2016 | Gray et al. | |
| 9,465,477 B2 | 10/2016 | Rosenberg et al. | |
| 2001/0044588 A1 | 11/2001 | Mault | |
| 2002/0163827 A1 | 11/2002 | Mullarkey et al. | |
| 2002/0167831 A1 | 11/2002 | Mullarkey et al. | |
| 2003/0185080 A1 | 10/2003 | Mullarkey et al. | |
| 2003/0234039 A1 | 12/2003 | Shajii et al. | |
| 2003/0234044 A1 | 12/2003 | Shajii et al. | |
| 2003/0234045 A1 | 12/2003 | Shajii et al. | |
| 2003/0234046 A1 | 12/2003 | Shajii et al. | |
| 2003/0234047 A1 | 12/2003 | Shajii et al. | |
| 2003/0234048 A1 | 12/2003 | Shajii et al. | |
| 2003/0236592 A1 | 12/2003 | Shajii et al. | |
| 2003/0236638 A1 | 12/2003 | Shajii et al. | |
| 2003/0236643 A1 | 12/2003 | Shajii et al. | |
| 2004/0019259 A1 | 1/2004 | Brown et al. | |
| 2004/0133120 A1 | 7/2004 | Frei et al. | |
| 2004/0223397 A9 | 11/2004 | Mullarkey et al. | |
| 2004/0256003 A1 | 12/2004 | Shajii et al. | |
| 2005/0004500 A1 | 1/2005 | Rosser et al. | |
| 2005/0066407 A1 | 3/2005 | Delaney | |
| 2005/0096513 A1 | 5/2005 | Ozguz et al. | |
| 2005/0131317 A1 | 6/2005 | Oddsson et al. | |
| 2005/0148904 A1 | 7/2005 | Mimura et al. | |
| 2005/0165284 A1 | 7/2005 | Gefen | |
| 2005/0190531 A1 | 9/2005 | Gall et al. | |
| 2005/0197540 A1 | 9/2005 | Liedtke | |
| 2005/0201135 A1 | 9/2005 | Mullarkey et al. | |
| 2006/0016255 A1 | 1/2006 | Haselhurst et al. | |
| 2006/0052678 A1 | 3/2006 | Drinan et al. | |
| 2006/0110049 A1 | 5/2006 | Liang et al. | |
| 2006/0173642 A1 | 8/2006 | Shajii et al. | |
| 2006/0282017 A1 | 12/2006 | Avni et al. | |
| 2007/0038042 A1 | 2/2007 | Freeman et al. | |
| 2007/0173903 A1 | 7/2007 | Goren et al. | |
| 2007/0203533 A1 | 8/2007 | Goren et al. | |
| 2007/0227762 A1 | 10/2007 | Yang et al. | |
| 2007/0234825 A1 | 10/2007 | Loomis et al. | |
| 2007/0250286 A1 | 10/2007 | Duncan et al. | |
| 2007/0282562 A1 | 12/2007 | Schwartz et al. | |
| 2008/0091306 A1 | 4/2008 | Shajii et al. | |
| 2008/0098820 A1 | 5/2008 | Morsch et al. | |
| 2008/0167580 A1 | 7/2008 | Avni et al. | |
| 2008/0171957 A1 | 7/2008 | Connolly et al. | |
| 2008/0287832 A1* | 11/2008 | Collins | ............... A43B 3/0005 600/587 |
| 2008/0306352 A1 | 12/2008 | Beiswenger et al. | |
| 2008/0306407 A1 | 12/2008 | Taylor | |
| 2008/0307899 A1 | 12/2008 | Von Lilienfeld-Toal et al. | |
| 2009/0036885 A1 | 2/2009 | Gregg | |
| 2009/0048070 A1 | 2/2009 | Vincent et al. | |
| 2009/0069865 A1 | 3/2009 | Lasko et al. | |
| 2009/0070939 A1 | 3/2009 | Hann | |
| 2009/0099471 A1 | 4/2009 | Broadley et al. | |
| 2009/0156988 A1 | 6/2009 | Ferren et al. | |
| 2009/0157054 A1 | 6/2009 | Ferren et al. | |
| 2009/0157055 A1 | 6/2009 | Ferren et al. | |
| 2009/0157056 A1 | 6/2009 | Ferren et al. | |
| 2009/0157057 A1 | 6/2009 | Ferren et al. | |
| 2009/0157058 A1 | 6/2009 | Ferren et al. | |
| 2009/0157171 A1 | 6/2009 | Ferren et al. | |
| 2009/0163856 A1 | 6/2009 | Ferren et al. | |
| 2009/0209830 A1 | 8/2009 | Nagle et al. | |

(56) References Cited

U.S. PATENT DOCUMENTS

| | | |
|---|---|---|
| 2009/0234249 A1 | 9/2009 | Randolph |
| 2009/0267783 A1 | 10/2009 | Vock et al. |
| 2009/0281412 A1 | 11/2009 | Boyden et al. |
| 2009/0281413 A1 | 11/2009 | Boyden et al. |
| 2009/0284378 A1 | 11/2009 | Ferren et al. |
| 2009/0287093 A1 | 11/2009 | Ferren et al. |
| 2009/0287094 A1 | 11/2009 | Ferren et al. |
| 2009/0287101 A1 | 11/2009 | Ferren et al. |
| 2009/0287109 A1 | 11/2009 | Ferren et al. |
| 2009/0287110 A1 | 11/2009 | Ferren et al. |
| 2009/0287120 A1 | 11/2009 | Ferren et al. |
| 2009/0287191 A1 | 11/2009 | Ferren et al. |
| 2009/0292195 A1 | 11/2009 | Boyden et al. |
| 2009/0292212 A1 | 11/2009 | Ferren et al. |
| 2009/0292213 A1 | 11/2009 | Ferren et al. |
| 2009/0292214 A1 | 11/2009 | Ferren et al. |
| 2009/0292222 A1 | 11/2009 | Ferren et al. |
| 2009/0293319 A1 | 12/2009 | Avni |
| 2009/0318802 A1 | 12/2009 | Boyden et al. |
| 2010/0004566 A1 | 1/2010 | Son et al. |
| 2010/0036209 A1 | 2/2010 | Ferren et al. |
| 2010/0036263 A1 | 2/2010 | Ferren et al. |
| 2010/0036268 A1 | 2/2010 | Ferren et al. |
| 2010/0036269 A1 | 2/2010 | Ferren et al. |
| 2010/0081890 A1 | 4/2010 | Li et al. |
| 2010/0107770 A1 | 5/2010 | Serban et al. |
| 2010/0201650 A1 | 8/2010 | Son |
| 2010/0210975 A1 | 8/2010 | Anthony, III et al. |
| 2010/0210983 A1 | 8/2010 | Baker et al. |
| 2010/0210988 A1 | 8/2010 | Dallison et al. |
| 2010/0249553 A1 | 9/2010 | MacLaughlin |
| 2010/0292600 A1 | 11/2010 | Dibenedetto et al. |
| 2010/0324743 A1 | 12/2010 | Shajii et al. |
| 2011/0015498 A1 | 1/2011 | Mestrovic et al. |
| 2011/0054270 A1 | 3/2011 | Derchak |
| 2011/0054359 A1 | 3/2011 | Sazonov et al. |
| 2011/0054809 A1 | 3/2011 | Templeman |
| 2011/0087445 A1 | 4/2011 | Sobolewski |
| 2011/0178375 A1 | 7/2011 | Forster |
| 2011/0184257 A1 | 7/2011 | Boll et al. |
| 2011/0230732 A1 | 9/2011 | Edman et al. |
| 2011/0263950 A1 | 10/2011 | Larson et al. |
| 2011/0319787 A1 | 12/2011 | Lamoise et al. |
| 2012/0004566 A1 | 1/2012 | Zhang et al. |
| 2012/0174992 A1 | 7/2012 | Shajii et al. |
| 2012/0245439 A1 | 9/2012 | Andre et al. |
| 2013/0041235 A1 | 2/2013 | Rogers et al. |
| 2013/0066168 A1 | 3/2013 | Yang et al. |
| 2013/0102930 A1 | 4/2013 | Connor |
| 2013/0120157 A1 | 5/2013 | Geva |
| 2013/0137943 A1 | 5/2013 | Pinto Rodrigues |
| 2013/0271278 A1 | 10/2013 | Duesterhoft et al. |
| 2014/0005618 A1 | 1/2014 | Locke et al. |
| 2014/0150571 A1 | 6/2014 | Kuniyoshi et al. |
| 2015/0057562 A1 | 2/2015 | Linders et al. |
| 2015/0177081 A1 | 6/2015 | Steier |

FOREIGN PATENT DOCUMENTS

| | | |
|---|---|---|
| CA | 2376162 A1 | 1/2001 |
| CA | 2411394 A1 | 12/2001 |
| CA | 2528218 A1 | 12/2004 |
| CA | 2604633 A1 | 10/2005 |
| CA | 2538940 A1 | 6/2006 |
| CA | 2590870 A1 | 7/2006 |
| CA | 2583034 A1 | 9/2007 |
| CA | 2654388 A1 | 1/2008 |
| CA | 2656733 A1 | 1/2008 |
| CA | 2696932 A1 | 2/2009 |
| CA | 2701238 A1 | 4/2009 |
| CA | 2744215 A1 | 6/2010 |
| CA | 2753063 A1 | 10/2010 |
| CA | 2767292 A1 | 1/2011 |
| CA | 2786524 A1 | 7/2011 |
| CA | 2815963 A1 | 5/2012 |
| EP | 1207785 A1 | 5/2002 |
| EP | 1 488 744 A1 | 12/2004 |
| EP | 0 835 045 B1 | 6/2006 |
| EP | 1 785 706 A1 | 5/2007 |
| EP | 2143090 A1 | 1/2010 |
| GB | 2 445 760 A | 7/2008 |
| JP | 8-238275 A | 9/1996 |
| WO | WO 01/00089 A1 | 1/2001 |
| WO | WO 01/36051 A2 | 5/2001 |
| WO | WO 03/079898 A1 | 10/2003 |
| WO | WO 03/086235 A2 | 10/2003 |
| WO | WO 2007/106040 A1 | 9/2007 |
| WO | WO 2008/088985 A2 | 7/2008 |
| WO | 2009/005373 A1 | 1/2009 |
| WO | WO 2009/132465 A1 | 11/2009 |
| WO | WO 2010/096691 A2 | 8/2010 |
| WO | WO 2010/119441 A2 | 10/2010 |
| WO | WO 2011/091517 A1 | 8/2011 |
| WO | 2013/131120 A1 | 9/2013 |

OTHER PUBLICATIONS

U.S. Office Action mailed Mar. 12, 2014 in co-pending U.S. Appl. No. 13/284,592.

U.S. Office Action mailed Oct. 10, 2014 in co-pending U.S. Appl. No. 13/284,592.

U.S. Office Action mailed Jul. 2, 2015 in co-pending U.S. Appl. No. 13/284,592.

U.S. Office Action mailed Dec. 9, 2015 in co-pending U.S. Appl. No. 13/284,592.

English translation of Notice of Rejection issued Feb. 16, 2016 in Japanese Patent Application No. 2013-535218.

International Search Report issued Feb. 1, 2012 in PCT/CA2011/001200 with Written Opinion.

Notice of Acceptance issued Jul. 1, 2015 in New Zealand Patent Application No. 611197.

Australian Examination Report issued May 13, 2015 in Patent Application No. 2011320072.

Office Action issued Jun. 30, 2015 in Japanese Patent Application No. 2013-535218 (with English language translation).

Extended European Search Report issued Mar. 3, 2014 in Patent Application No. 11835396.0.

Darrell Etherington, "Apple Patents Smart Shoes That Feature Embedded Sensors, and Alarms for When You Need New Ones" TechCrunch Survey, http://techcrunch.com/2013/01/24/apple-patents-smart-shoes-that-feature-embedded-sensors-and-alarms-for-when-you-need-new-ones/ , Posted Jan. 24, 2013, 8 Pages (corresponds to US 2009/0267783 A1).

International Search Report and Written Opinion issued Aug. 19, 2014 in corresponding PCT/CA2014/050471.

"Electronic sensor technologies for wounds", Delta, Path-monitoring, Rev. Sep. 26, 2012, pp. 4-23 with cover pages.

"Smart bandage", The Engineer, vol. 10, Apr. 6, 2009, 2 Pages.

Augustin Grillet, et al., "Optical fiber sensors embedded into medical textiles for healthcare monitoring", IEEE Sensors Journal, vol. 8, No. 7, Jul. 2008, pp. 1215-1222.

Office Action dated Jun. 28, 2016, in co-pending U.S. Appl. No. 13/284,592.

Office Action dated Dec. 22, 2016, in co-pending U.S. Appl. No. 13/284,592.

Notice of Allowance dated Aug. 2, 2016, in Japanese Patent Application No. 2013-535218 (with English-language translation).

Notice of Acceptance dated May 5, 2016, in Australian Patent Application No. 2011320072.

Office Action dated May 12, 2017, in Canadian Patent Application No. 2,813,656.

Extended European Search Report dated Jan. 19, 2017, in Patent Application No. 14801355.0.

International Preliminary Report on Patentability and Written Opinion of the International Searching Authority dated Dec. 3, 2015, in PCT/CA2014/050471, filed May 21, 2014.

International Preliminary Report on Patentability and Written Opinion of the International Searching Authority dated May 10, 2013, in PCT/CA2011/001200, filed Oct. 28, 2011.

(56) References Cited

OTHER PUBLICATIONS

Office Action dated May 30, 2017, in co-pending U.S. Appl. No. 13/284,592.
Gafurov et al., "Biometric Gait Authentication Using Accelerometer Sensor," Journal of Computers, Nov. 2006, vol. 1 (7), pp. 51-59.
Huang et al., "Gait Modeling for Human Identification," Robotics and Automation, IEEE International Conference on, Apr. 10-14, 2007, pp. 4833-4838.
Kong et al., "A Gait Monitoring System Based on Air Pressure Sensors Embedded in a Shoe," IEEE/ASME Transactions on Mechatronics, Jun. 2009, vol. 14 (3), pp. 358-370.
Yamakawa et al., "Biometric Personal Identification Based on Gait Pattern Using Both Feet Pressure Change," World Automation Congress, Sep. 2008, pp. 1-6.

\* cited by examiner

PRESSURE DATA ACQUISITION ASSEMBLY

CROSS-REFERENCE TO RELATED APPLICATIONS

This application claims the benefit of priority of U.S. Provisional Patent Application No. 61/825,871, entitled "ELECTRONIC BANDAGE AND DATA ACQUISITION ASSEMBLY" filed May 21, 2013, which is hereby incorporated by reference in its entirety.

FIELD

The present disclosure relates to pressure sensors for use on individuals. More particularly, the present disclosure relates to a pressure data acquisition assembly and methods of use thereof.

BACKGROUND

Medical bandages equipped with electronic monitoring capabilities are known. U.S. Pat. No. 7,597,676, for example, discloses a malleolar pad which provides the physician with an electronic capability to measure and adjust compressive forces applied to ankle injuries. Known electronic bandages commonly include a bandage component and an electronic component capable of monitoring certain aspects of a skin injury. Patients who lack normal mobility and patients whose peripheral sensory perception is compromised (e.g. due to an underlying medical condition, etc.) may be predisposed to fail to respond normally to detrimental levels of skin pressure distribution. This in turn can result in a variety of medical conditions including focal ischemia, and in more serious cases, pressure necrosis, ulceration, infection, and gangrene. In the most extreme cases, this necessitates surgical procedures, including amputation.

SUMMARY

Known pressure data acquisition assemblies are typically deficient in adapting to changing conditions at a surface on which pressure is being measured. Furthermore, pressure data acquisition assemblies (e.g. those designed to monitor pressure ulcers) are often unsuitable for use in conjunction with non-planar or irregularly shaped skin areas of the body (e.g. as the sacral bone area, joints or other non-stationary skin areas of the body, etc.). Pressure on these areas of the body can vary substantially, both locally within an area of the skin and/or temporally. Consequently, data readings obtained by previous electronic bandages from these areas are generally inaccurate, resulting in suboptimal patient care. In addition, depending on the condition of a surface that a pressure sensor is attached to (e.g. wounded, injured, sensitive, etc.), the operation of the pressure sensor may be directed to lower or higher pressures, or other parameters may be adjusted. There exists, therefore, a need for a pressure data acquisition assembly which may be used with accuracy on a variety of surfaces on an individual's body, and which can be used under a wide variety of conditions.

The present disclosure relates to a pressure data acquisition assembly.

In a first aspect, the present disclosure provides a method and assembly for acquiring pressure data. A pressure sensor is applied to a target surface on an individual. A calibrator and a processing element are in communication with the pressure sensor. Processing element receives pressure data and provides an integrated pressure value over a measurement time period. The integrated pressure value is compared to an alert value and to a change condition value. Where an alert value is exceeded, an alert is transmitted to an output device for display. Where a change condition value is exceeded, a measurement parameter of the pressure sensor is changed, or the calibrator is applied to the pressure sensor to recalibrate the pressure sensor to a recalibrated pressure range.

In a further aspect, herein provided is a pressure data acquisition assembly including a support web for applying to a target surface of a body of an individual; a first pressure sensor connected to the support web for sensing at a first frequency a first pressure applied to the target surface; a calibrator in operative communication with the first pressure sensor for calibrating the first pressure sensor to a first pressure range within which the first pressure sensor senses the first pressure; and a processing element in operative communication with the first pressure sensor for receiving first pressure signals corresponding to values of the first pressure from the first pressure sensor at the first frequency, and with the calibrator for recalibrating the first pressure sensor. The processing element includes a computer readable memory for storing measurement parameters comprising a first threshold value corresponding to a first threshold pressure, a first measurement time period, a first alert value, and a first change condition; and a processor in operative communication with the computer readable memory for accessing the measurement parameters, comparing the first pressure to the first threshold pressure to provide a first comparative pressure, integrating the first comparative pressure over the first time measurement period to provide a first integrated pressure, comparing the first integrated pressure with the first alert value to determine a first alert status, comparing the first integrated pressure with the first change condition to determine a first change status, and changing at least one measurement parameter or recalibrating the first pressure sensor to a first recalibrated pressure range, according to the first change status. An output device is in communication with the processing element for receiving signals comprising data from the processing element and displaying the data.

In an embodiment, the assembly includes a second pressure sensor for sensing at a second frequency a second pressure applied to the target surface. The calibrator is further in operative communication with the second pressure sensor for calibrating the second pressure sensor.

The processing element is in operative communication with the second pressure sensor for receiving second pressure signals corresponding to values of the second pressure from the second pressure sensor at the second frequency, and with the calibrator for recalibrating the second pressure sensor. The measurement parameters further comprise a second threshold value corresponding to a second threshold pressure, a second measurement time period, a second alert value, and a second change condition. The processing element is further for comparing the second normalized pressure to a second threshold pressure value to determine a second comparative pressure. The processor is in operative communication with the computer readable memory for accessing the measurement parameters, comparing the second pressure to the second threshold pressure to provide a second comparative pressure, integrating the second comparative pressure with time over the second time measurement period to provide a second integrated pressure, comparing the second integrated pressure with the second alert value to determine a second alert status, comparing the second integrated pressure with the second change condition to determine a second change status, and changing at least one measurement parameter or recalibrating at least one of the first pressure sensor to a first recalibrated pressure range and the second pressure sensor to a second recalibrated pressure range, according to the second change status. In an embodiment, the data comprises data of the first and second comparative pressures and the relative locations of the first and second pressure sensors on the target area, and the data is displayed visually. In an embodiment, the first frequency and the second frequency are substantially equal. In an embodiment, the first pressure range and the second pressure range are substantially equal. In an embodiment, the calibrator is for calibrating the first pressure sensor and the second pressure sensor with a single input action. In an embodiment, the first recalibration pressure range and the second recalibration pressure range are substantially equal. In an embodiment, the first threshold pressure and the second threshold pressure are substantially equal.

In an embodiment, the assembly includes a biological parameter sensor connected to the support web for sensing at a biological parameter frequency a biological parameter of the target surface. The processing element is in operative communication with the biological parameter sensor for receiving biological parameter signals in a biological parameter value range corresponding to biological parameter values at the biological parameter frequency. The measurement parameters further comprise a biological threshold value corresponding to a threshold biological parameter value, a biological parameter measurement time period, a biological parameter alert value, and a biological parameter change condition. The processor is in operative communication with the computer readable memory for accessing the measurement parameters, comparing the biological parameter values to the threshold biological parameter value to provide a comparative biological parameter value, integrating the comparative biological parameter value over the biological parameter time measurement period to provide an integrated biological parameter value, comparing the biological parameter value with the biological parameter alert value to determine a biological parameter alert status, comparing the biological parameter integrated pressure with the biological parameter change condition to determine a biological parameter change status, and changing at least one measurement parameter or recalibrating the first pressure sensor to the first recalibrated pressure range, according to the biological parameter change status. The output device is in communication with the processing element for displaying the comparative biological parameter value. In an embodiment, the processing element is in operative communication with the calibrator for recalibrating the biological parameter sensor to a recalibrated biological parameter range according to the biological parameter change status. In an embodiment, the assembly includes a feedback element connected to the support web for performing an action on the target surface for performing the action in response to the biological parameter alert status. In an embodiment, the biological parameter is temperature. In an embodiment, the biological parameter is pH. In an embodiment, the biological parameter is humidity. In an embodiment, the biological parameter is muscle activity.

In an embodiment, the assembly includes a feedback element connected to the support web for performing an action on the target surface for performing the action in response to the first alert status.

In an embodiment, the support web comprises a treatment portion for contacting sensitive skin.

In an embodiment, the support web comprises an adhesive material for adhering the support web to the target surface.

In an embodiment, the processing element further comprises a timer for measuring a total time that the support web is applied to the target surface; and the output device is for displaying the total time In an embodiment, the processing element further comprises a timer for computing a time period wherein, following a time interval of application of the first pressure to the target surface, no pressure is applied to the target surface, and wherein the output device is for displaying the time period wherein no external pressure is applied.

In an embodiment, at least a portion of the output device is positioned apart from the support web.

In an embodiment, the first pressure sensor comprises a plurality of sensor elements. In an embodiment, the sensor elements are arranged to define a generally circular area around the pressure sensor. In an embodiment, the sensor elements comprise lobe shaped sensors elements.

In an embodiment, the threshold pressure value is between about 0 and about 80 mm Hg. In an embodiment, the threshold pressure value is between about 25 and about 35 mm Hg.

In an embodiment, the first frequency is between about 0.5 Hz and about 100 Hz. In an embodiment, the first frequency is between about 0.5 Hz and about 25 Hz.

In a further aspect, the present disclosure provides a method of acquiring pressure data including: applying a first pressure sensor to a target surface of a body of an individual; sensing at a first frequency a first pressure applied to the target surface; calibrating the first pressure sensor to a first pressure range within which the first pressure sensor senses the first pressure; providing first measurement parameters comprising a first threshold value corresponding to a first threshold pressure, a first measurement time period, a first alert value, and a first change condition; comparing the first pressure to the first threshold pressure to provide a first comparative pressure; integrating the first comparative pressure over the first time measurement period to provide a first integrated pressure; comparing the first integrated pressure with the first alert value to determine a first alert status; comparing the first integrated pressure with the first change condition to determine a first change status; changing at least one measurement parameter or recalibrating the first pressure range to the first recalibrated pressure range, according to the first change status; and displaying at least one of the first integrated pressure, the first alert status, and the first change status.

In an embodiment, the method includes applying a second pressure sensor to the target surface; sensing at a second frequency a second pressure applied to the target surface; calibrating the second pressure sensor to a second pressure range within which the second pressure sensor senses the second pressure; providing second measurement parameters comprising a second threshold value corresponding to a second threshold pressure, a second measurement time period, a second alert value, and a second change condition; comparing the second pressure to the second threshold pressure to provide a second comparative pressure; integrating the second comparative pressure over the second time measurement period to provide a second integrated pressure; comparing the second integrated pressure with the second alert value to determine a second alert status; comparing the second integrated pressure with the second change condition to determine a second change status; changing at least one measurement parameter or recalibrating the second pressure range to the second recalibrated pressure range, according to the second change status; and displaying at least one of the second integrated pressure, the second alert status, and the second change status. In an embodiment, displaying the first integrated pressure, the first alert status, the second integrated pressure, and the second alert status comprises visually displaying data of the first and second comparative pressures and the relative locations of the first and second pressure sensors on the target area.

In an embodiment, the method includes applying a biological parameter sensor to the target surface; sensing at a biological parameter frequency a biological parameter at the target surface; providing measurement parameters comprising a biological parameter threshold value corresponding to a biological parameter threshold, a biological parameter measurement time period, a biological parameter alert value, and a biological parameter change condition; comparing the biological parameter to the biological parameter threshold pressure to provide a comparative biological parameter value; integrating the comparative biological parameter over the biological parameter time measurement period to provide an integrated biological parameter pressure; comparing the integrated biological parameter with the biological parameter alert value to determine a biological parameter alert status; comparing the integrated biological parameter with the biological parameter change condition to determine a biological parameter change status; changing at least one measurement parameter or recalibrating the first pressure range to the first recalibrated pressure range, according to the biological parameter change status; and displaying at least one of the integrated biological parameter value, the biological parameter alert status, and the biological parameter change status.

In a further aspect, the present disclosure provides use of a pressure data acquisition assembly in the diagnosis or treatment of pressure ulcers.

In a further aspect, the present disclosure provides use of a pressure data acquisition assembly on an irregular target surface.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached figures in which like numerals designate like or similar features.

DETAILED DESCRIPTION

A pressure data acquisition assembly is disclosed herein. The assembly includes a support web (e.g. a bandage, etc.), a pressure sensor coupled to the support web, and an output device in communication with the pressure sensor. Other sensors in addition to the pressure sensor may be connected to the support web.

The pressure sensor senses pressure exerted on an external surface area of an individual's body (e.g. an injured external surface of the body, an external surface area of the body that may be prone to injury, etc.). The output device receives data relating to the pressure and records or displays information for a user of the assembly (e.g. a patient, a healthcare provider, etc.). The assembly may be used for monitoring pressure in an individual experiencing compromised sensory perception (e.g. due to peripheral neuropathy, etc.), and for individuals who lack normal mobility (e.g. comatose patients, individuals who use a wheel chair, etc.).

The assembly monitors a target surface on the body surface on a continuous basis and dynamically presents relevant information to the user. The assembly may be capable of immediately notifying the user with an alert signal when skin or underlying tissue is compromised, or at risk to be compromised. This notification facilitates early corrective intervention and mitigates tissue damage.

The assembly includes an active calibrator for changing the range of pressure values detected by the assembly. The target surface may be non-planar or irregularly shaped (e.g. an area comprising a bony prominence such as the sacral bone area, etc.), and may be on a portion of the body that is subject to reshaping during body movement (e.g. a joint area, etc.). A user can recalibrate the pressure range or change measurement parameters relevant to pressure sensing and alerts. When a change condition is met, recalibration or changing measurement parameters occurs automatically.

Pressure Data Acquisition Assembly

Figure 1:
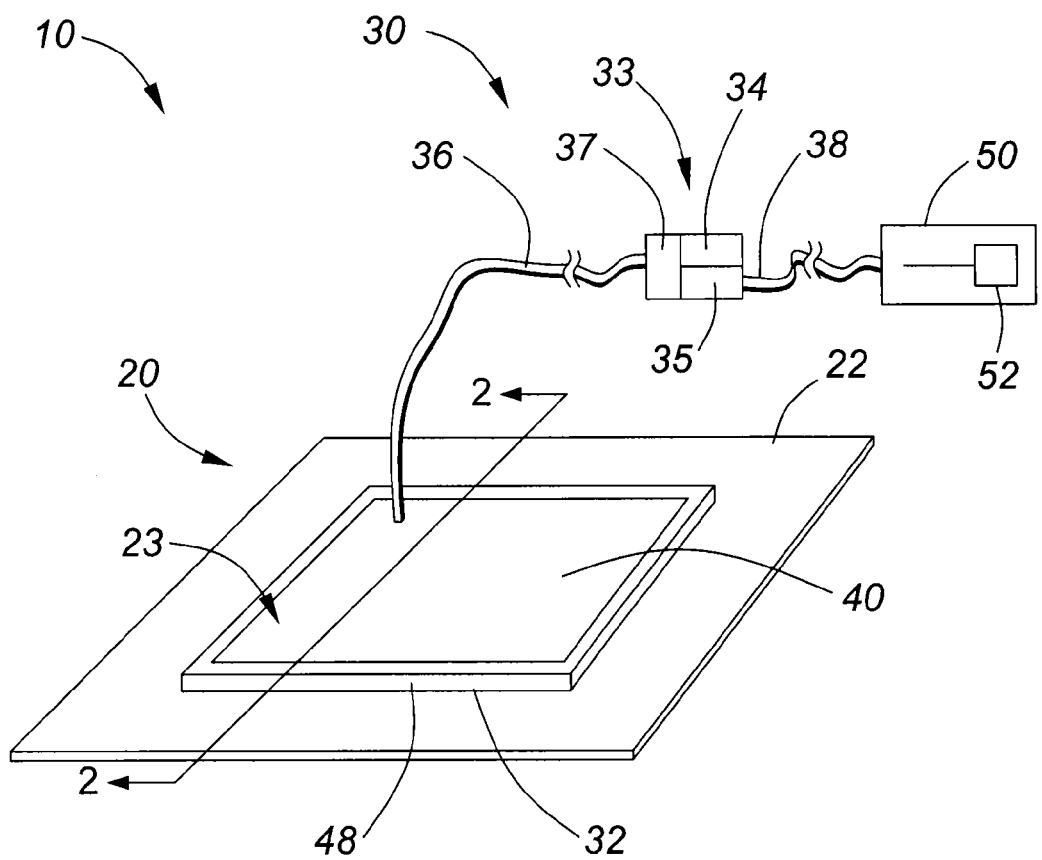
FIG. 1 is a perspective view of a pressure data acquisition assembly.

FIG. 1 is a pressure data acquisition assembly 10. The assembly 10 includes a support web 20 and an electronic controlling portion 30. The support web 20 includes a support portion 22 with a sensing portion 23 defined within the support portion 22. The electronic controlling portion 30 includes an input element 32 associated with the sensing portion 23. The input element 32 includes a pressure sensor 40 for sensing a pressure applied to the sensing portion 23.

The input element 32 generates a signal in response to pressure application and is in operative communication with a processing element 33 through a first connection 36 for transmission of the signal from the input element 32 to the processing element 33 (the first connection 36 is shown as a wired connection, but any suitable signal transmitting connection may be applied). The processing element 33 is in operative communication with an output device 50 through a second connection 38 for transmitting output signals including data of a comparative pressure (see FIG. 4 below) from the processing element 33 to the output device 50 (the second connection 38 is shown as a wired connection, but any connection suitable for transmission of the output signals generated by the processor may be applied). The support web 20 may be removable from the electronic controlling portion 30 for reuse of the electronic controlling portion 30, or the processing element 33 may be removable from the input element 32 and support web 20 for reuse of the processing element 33.

Support Web

The support web 20 includes the support portion 22. The support portion 22 provides a support substrate for the input element 32 and may be relatively strong, thin, stretchable, and capable of following the contours of a target surface of an individual on whom the bandage 20 will be placed. The target surface may be an external surface of a human or other body that is injured, prone to injury, wounded, or an area otherwise to be monitored by the pressure data acquisition assembly 10. The pressure sensor 40 and support portion 22 substantially conform to the target surface.

The support portion 22 may be constructed using fabric or a biocompatible polymeric material (e.g. polyurethane, polyolefins, vinyl polyethylene acetate, textile, non-woven fabrics, rubber, other suitable materials, etc.). The support web 20 may be part of a larger assembly, including a bandage (e.g. the bandage and pressure data acquisition assembly 111 of FIG. 7) diaper, undergarments, bed sheet, mattress, etc.

Input Element

The electronic controlling portion 30 includes the input element 32. The input element 32 includes a pressure sensor 40 for repeatedly and periodically measuring pressure or force exerted on the target surface during a time interval. The input element 32 may also include other sensors to sense other suitable biological parameters. A signal corresponding to the measured pressure, and if applicable, any other biological parameters, is provided to the processing element 33 from the input element 32. The input element 32 may include an amplifier (not shown) to amplify the signal provided by the pressure sensor 40 prior to the signal being communicated to the processing element 33. The input element 32 and the pressure sensor 40 may receive power through the first connection 36 (e.g. from a battery on the electronic controlling portion 30, from a plug-in at the output device 50 where the second connection 38 is a wired connection, etc.). Power to the input element 32, the pressure sensor 40, or both, may be periodically disconnected to conserve battery or otherwise reduce power consumption.

Figure 2:
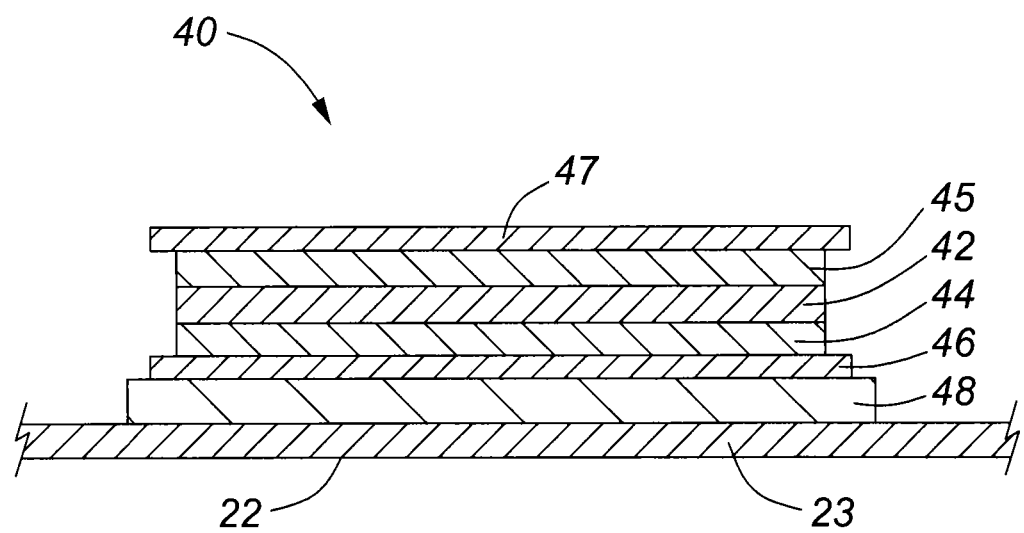
FIG. 2 is a cross-sectional view along of a pressure sensor of the pressure data acquisition assembly of FIG. 1 along plane 2-2.

FIG. 2 is a cross-section of the pressure sensor 40. The pressure sensor 40 includes a piezoactive material 42 for converting changes in the application of pressure to the pressure sensor 40 into an electrical signal. The piezoactive material 42 is between a first flexible electrode 44 and a second flexible electrode 45. A first flexible surface layer 46 is positioned externally to the first flexible electrode 44 and a second flexible surface layer 47 is positioned externally to the second flexible electrode 45. A first substrate carrier layer 48 is positioned externally to the first flexible surface layer 46. The first substrate carrier layer 48 is connected to the support portion 22 at the sensing portion 23.

The piezoactive material 42 may include a piezoresistive material (e.g. piezoresistive ink, etc.), a piezocapacitative material (e.g. dielectric glass or other dielectric material, etc.), or a piezoelectric material (e.g. piezoelectric ink, etc.). Piezoresistive inks are inks capable of conducting electricity and may include a variety of metals (e.g. copper, silver, gold, graphite or other conductive carbon, or tin oxide or other conductive ceramics, polypyrole or other conducting polymers, or mixtures thereof, etc.). Where the piezoactive material 42 includes piezoresistive material, modulation of the application of pressure to the pressure sensor 40 results in changes to the resistance of the piezoresistive material 42, which in turn results in the signal corresponding to the measured pressure being sent to the processing element 33.

The flexible electrodes 44, 45 generally include conductive metals, (e.g. copper, silver, aluminum, gold, etc.). The first flexible electrode 44 may be manufactured of the same material as the second flexible electrode 45 or of a different material.

The flexible surface layers 46, 47 support and protect the piezoactive material 42 and flexible electrodes 44, 45. The flexible surface layers 46, 47 may be composed of any suitable material (e.g. polyethelene terephthalate (PET), also known as Mylar™, etc.). The material of the flexible surfaces layers 46, 47 is selected to be an effective insulator and to be compatible with the flexible electrodes 44, 45.

The substrate carrier layer 48 is prepared from a material that maintains an appropriate elasticity and durometer values and is compatible both with the first flexible surface layer 46 and the sensing portion 23 (e.g. thermoplastic polyurethane for use with a PET flexible surface layers 46, etc.).

The pressure sensor 40 may be thin (e.g. ranging from about 50 µm to about 1000 µm, less than about 200 µm, etc.). The thin and flexible nature of the pressure sensor 40 facilitates conforming to the target surface to which the support web 20 is applied. Substantial conformity with the target surface facilitates measurement of pressure and other biological parameters on non-planar and irregular target surfaces.

The pressure sensor 40 may be manufactured using a multi-step printing process, allowing for selection of the shape of the pressure sensor 40, which may be round, oval, lobe shaped, wedge shaped, or any other suitable shape. For example, the first flexible surface layer 46 may be printed, followed by the first flexible electrode 44, the piezoactive material 42, the second flexible electrode 45, and the second flexible surface layer 47.

Alternatively, a first portion of the sensor 40 may be fabricated and assembled with a second portion of the sensor 40. For example, the first portion may include the first flexible surface layer 46, the first flexible electrode 44, and the piezoactive material 42. The second portion may include the second flexible surface layer 47 and the second flexible electrode 45. The first and second portions may then be assembled and mounted onto the support web 20 (see FIG. 1).

Figure 3:
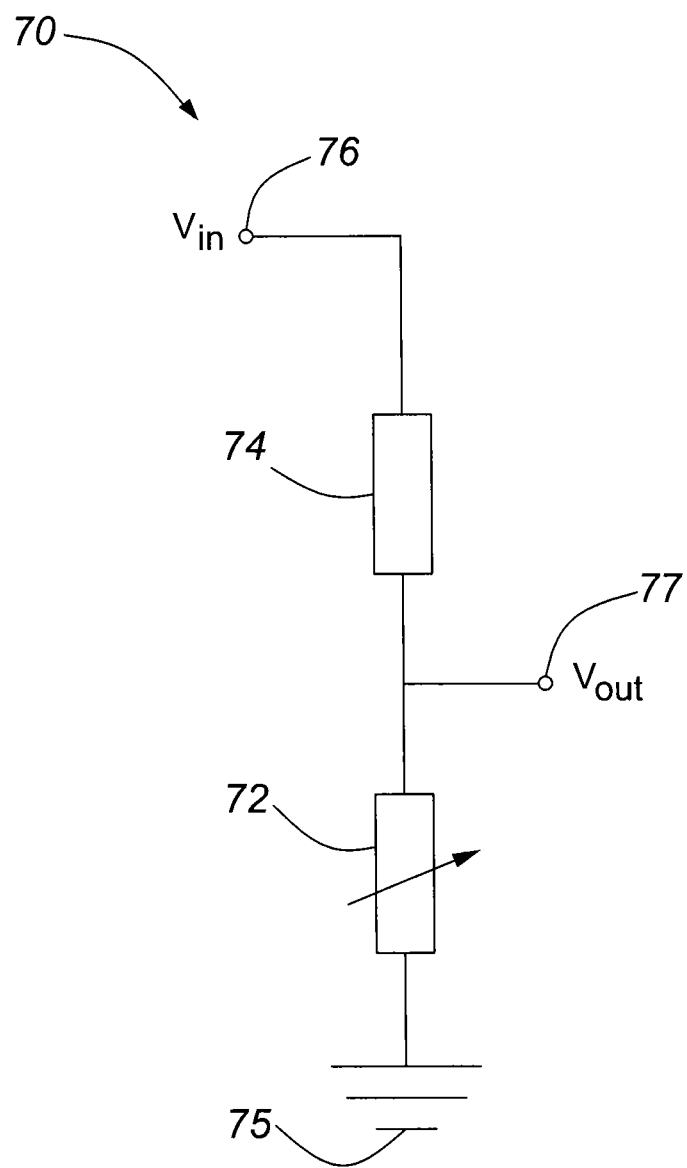
FIG. 3 is a schematic of a passive calibration electrical circuit for use with the sensor of FIG. 1.

FIG. 3 is an exemplary electrical circuit 70 for inclusion into the pressure sensor 40. The electrical circuit includes an adjustable sensor resistor 72. Where the piezoactive material 42 includes piezoresistive material, the adjustable sensor resistor 72 includes the piezoresistive material, which changes resistance in response modulation of the application of pressure to the pressure sensor 40.

The adjustable sensor resistor 72 is electrically coupled in series between a constant resistor 74 and a ground 75. A voltage is applied between voltage points $V_{in}$ 76 and $V_{out}$ 77. The voltage is applied through a power supply (e.g. a battery, etc.). The applied voltage provides a voltage level defined by the resistors 72, 74 and the amperage of the current. As a result of a modulation in application of force on the piezoresistive material in the piezoactive material 42, the resistance in the adjustable sensor resistor 72 changes, and the voltage between $V_{in}$ 76 and $V_{out}$ 77 changes. This change can be measured and correlated to the modulation of the application of pressure to the pressure sensor 40.

Processing Element

The processing element 33 includes a processor 34 in operative communication with a computer readable memory 35 for accessing information in the computer readable memory 35.

The processor 34 (see FIG. 1) may include one or more microcontrollers, microprocessors, digital signal processors (DSPs), field programmable gate arrays (FPGAs), application specific integrated circuits (ASICs), or other suitable programmable devices. The processor 34 may also be in communication a peripheral devices (e.g. analog-to-digital (A/D) converters, serial or parallel digital input/output devices, other peripheral components or devices, etc.) upstream of the output device 50 (peripheral device not shown). The processor 34 accesses a program encoded on a computer readable memory 35 or other circuit for storing instructions for execution on the processor 34, or these instructions may be present on the processor 34.

The computer readable memory 35 includes a data store in electronic readable format. The data store includes a threshold pressure value and other measurement parameters. The data store may also include a threshold value for one or more other measured biological parameters. The data store may be organized in any suitable manner for storing, accessing, and retrieving data (e.g. databases, tables, files, lists, queues, directories, data storage devices, data serves, data storage media, etc.).

The computer readable memory 35 may include any storage component configured to be programmed with a value or state and maintain that value or state for access at a later time, and associated hardware and software. The computer readable memory 35 may store such value or state in any suitable memory (e.g. random access memory, read only memory (ROM), erasable programmable ROM (EPROM), electronically EPROM, application specific integrated circuit, etc.).

The processor 34 and the computer readable memory 35 may be positioned peripherally to the input element 32 and the sensing portion 23, and may be positioned peripherally to the support web 20, meaning that the processor 34 and the computer readable memory 35 are coupled to the input element 32, the sensing portion 23, or the support web 20, but separately housed. In some embodiments, one or both of the processor 34 and the computer readable memory 35 may be physically associated with the support web 20. Alternatively, one or both of the processor 34 and the computer readable memory 35 may be separately housed from the support web 20, which facilitates use of a support web 20 manufactured such that the processor 34, the computer readable memory 35, or both, can readily be decoupled from the input device 32 and re-used upon disposal of the support web 20 and input device 32.

Operation of Processing Element

Figure 4:
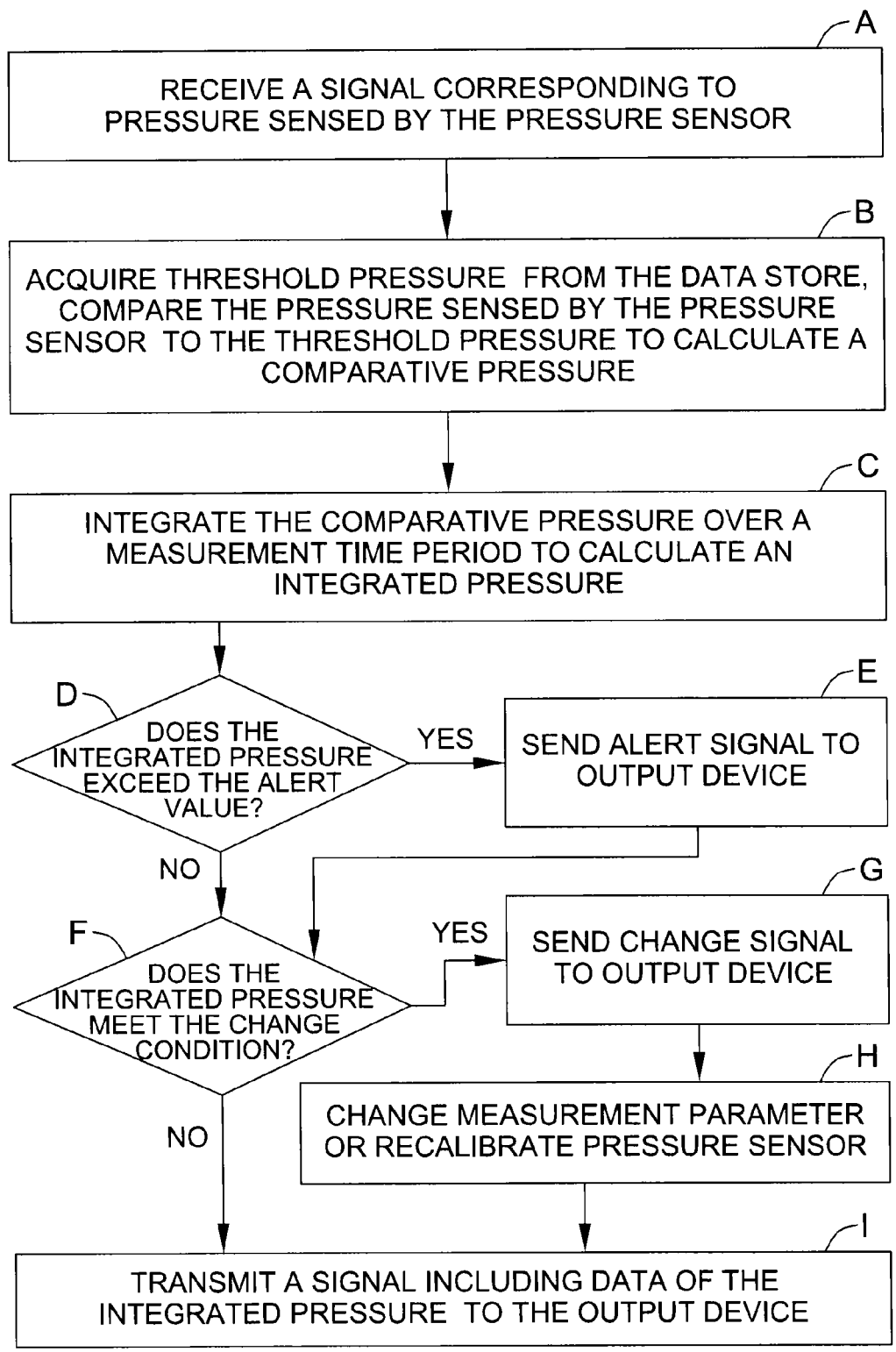
FIG. 4 is a flow chart of steps executed by a processor on the data acquisition assembly of FIG. 1.

FIG. 4 is a flowchart of a method for sensing pressure on the target surface. The processor 34 accesses and executes computer readable instructions for carrying out the steps of FIG. 4 (e.g. instructions resident on the computer readable memory 35, on the processor 34 itself, at a separate location transmitted wirelessly to the processor 34, etc.). The computer readable instructions cause the processor 34 to receive a signal corresponding to pressure sensed by the pressure sensor 40 (Step A), acquire the data corresponding to a threshold pressure value from the data store and compare the pressure in the signal to the to calculate a comparative pressure (Step B). The processor 34 integrates the comparative pressure over a measurement time period (e.g. 10 minutes, 15 minutes, etc.) to provide an integrated pressure (Step C), which is continuously updated on an ongoing basis (e.g. at the same frequency which the pressure sensor 40 senses pressure, etc.). The integrated pressure is compared against an alert value (Step D). If the integrated pressure is greater than the alert value, an alert signal is sent to the output device to display or change an alert status (Step E). The integrated pressure is also compared against a change condition (Step F). If the integrated pressure meets the change condition (e.g. integrated pressure has a greater value than a defined change value, integrated pressure is below a defined change value, etc.) a change signal is sent to the output device (Step G) and either change a measurement parameter applied by the processing element 33 is changed or an active calibrator 37 is applied to recalibrate the first pressure sensor 40 to a recalibrated pressure range (Step H). A signal corresponding to data of the integrated pressure is communicated from the processor 34 to the output device 50 (Step I).

The computer readable memory 35 includes data corresponding to measurement parameters including at least one threshold pressure value, at least one measurement time period, at least one alert value, and at least one change condition. Data corresponding to a plurality of any of the above measurement parameters may be stored in the computer readable memory 35 (e.g. a plurality of threshold pressure values for computing comparative pressures against different threshold pressure values, a plurality of measurement time periods, a plurality of alert values, a plurality of change conditions).

The threshold pressure value may be set at various values (e.g. between about 0 and about 80 mm Hg, between about 20 and about 40 mm Hg, between about 25 mm and 35 mm Hg, etc.). A threshold pressure value between about 25 mm and 35 mm Hg may facilitate use in the pressure data acquisition assembly 10 for application to a target surface that is not expected to receive substantial external pressure when the patient in normal resting condition. Lower threshold pressure values are useful where the target surface is wounded or otherwise sensitive, with higher threshold pressure values being more useful for target surfaces that are more resistant to damage from applied pressure.

The time period applicable to an integrated pressure may be lowered for comparing the integrated pressure over a smaller time period. This allows monitoring of changes over a shorter time frame, which facilitates monitoring of sensitive target surfaces.

The comparative pressures reflect, in a quantitative manner, the difference between a measured pressure value and the threshold pressure value. The comparative pressure may be relatively simple (e.g. subtraction of the threshold pressure value from the measured pressure value, etc.) or the comparative pressure may be more complex. The processor 34 integrates the comparative pressures recorded during a measurement time period, providing an integrated pressure. The integrated pressure may be express, for example, as a fraction of the pressure measurements which exceed the threshold pressure value during the measurement time period.

The processor 34 may be programmed to execute a timer function to measure the total time interval the support web 20 is applied continuously to the target surface. In these cases, the output device 50 would be capable of displaying the total time interval the support web 20 has been applied continuously the target surface. For example, an electronic clock may be automatically started upon first application of the support web 20 the target surface, and time kept for the entire duration the support web 20 is kept in place the target surface. The time data may be used by a physician or patient to interpret other data relating to the measurement of the pressure or other biological parameter provided by the output device 50. A log of pressure changes over time may have application in interpreting the sleep patterns of the individual on whom the target surface is located.

The processor 34 may further be configured to compute a time period wherein, following a time interval of application of external pressure to the target surface, no external pressure, or no external pressure in excess of the first value, the second value, or the alert value, is applied to said area. Data of the time period wherein no external pressure is applied may be communicated to the output device 50. This may provide data with respect to corrective action that has been taken following an indication that the target surface has received excess pressure.

Alert Value

An alert value may be defined and stored in the computer readable memory 35. The alert value is an integrated pressure value. Where the alert value is equaled or exceeded by the measured integrated pressure value, the processor 34 causes the output device 50 to communicate the alert signal to the user (see Step E in FIG. 4). Because the alert value is an integrated pressure value, it can be reached by high pressure readings for a short period of time, or lower pressure readings kept up consistently for a time. The alert value may for example alert individual on whom the target surface is located to mitigate formation of pressure ulcers, or direct turning of the individual by caregivers. Greater integrated pressure values can be used to determine how long and to what extent bloodflow has been restricted and the alert value indicates when pressure should be offloaded. The selected integrated pressure value would be based on the likelihood that further interruption of bloodflow will result in injury.

For example, the electronic controlling element 30 may be configured to measure pressure on the target surface with a periodicity of 4 Hz, during a time interval of 10 minutes. In this example, the data store includes a threshold pressure value of 30 mm Hg. If the pressure sensor has delivered 1000 readings exceeding 30 mM Hg to the processor 34 during the time interval, the total number of readings consists of 2400 readings (10 minutes at 4 Hz), while the fraction of readings exceeding the threshold pressure value computed by the processing element is 0.417. A defined fraction of pressure readings exceeding the threshold pressure value could be applied as the alert value, with fractions greater than the alert value resulting in the alert signal from the output device 50. The alert value could, for example, be 90% of measured pressure readings being greater than the threshold pressure value.

In another example, the threshold pressure value is between 35 and 50 mm Hg, and 3600 readings are taken during a 15 minute measurement time period at 4 Hz. This combination of measurement parameters is more suited to healthier individuals, or on a less sensitive target surface, than the above example with a 30 mm Hg threshold pressure value and 10 minute measurement time period. With a healthier individual or a less sensitive target surface, the alert value can be greater (i.e. through a greater threshold pressure value) and the measurement time period can be longer.

In another example, the processor 34 may be configured to provide different signals to the output device 50 based on the number of comparative pressure measurements exceeding a selected value, the selected value being analogous to the alert value. For example, the processor 34 may direct the output device 50 to send a first signal when the computed fraction of measurements that exceeds the threshold pressure value is lower than a first value (e.g. less than 25%, etc.), a second signal when the computed fraction of measurements that exceeds the threshold pressure value is higher than a second value (e.g. more than 75%, etc.), and the alert signal when the computed fraction of measurements that exceeds the threshold pressure value is greater than the alert value (e.g. more than 90%, etc.). These features allow a user of the pressure data acquisition assembly 10 to rapidly assess the degree to which the target surface is receiving stimuli in excess of the threshold pressure value (e.g. excess force, etc.), and take corrective or preventive action.

Where the electronic controlling element 34 and input element 32 are configured for continuous or regular monitoring, the output device 50 may be configured for immediate communication to a patient, physician or caregiver of an alert signal upon occurrence of an aggravating event to the target surface, facilitating timely intervention.

Change Condition

Where a plurality of one or more measurement parameters is available, a user may select a particular measurement parameter (e.g. a selected threshold pressure, time measurement period, alert value, or change condition). Similarly, the user may direct the active calibrator 37 to recalibrate the pressure sensor 40 to a recalibrated pressure range. A user may select an appropriate threshold pressure value, alert value, and measurement time period, and may recalibrate the pressure range when applying the support web 20 to the target surface. The user may select appropriate mild conditions (e.g. lower threshold pressure values, lower alert values, shorter measurement time periods etc.), and recalibrate the pressure sensor 40 to a lower pressure range, for sensitive target surfaces or use on individuals with poor circulation, etc. The user may select appropriate more severe conditions (e.g. higher threshold pressure values, higher alert values, longer measurement time periods etc.), and recalibrate the pressure sensor 40 to a higher pressure range, for target surfaces in good condition or use on target surfaces which are more robust.

The processor 34 may also direct a measurement parameter to change, or direct the active calibrator 37 to recalibrate the pressure sensor 40 to a different pressure range, in response to a change condition being met. For example, where a long period of alert values or other high integrated pressure values is sensed, the alert values may be lowered (or the threshold pressure values may be lowered, resulting in lowered alert values), or the time measurement period may be shortened. Similarly, the active calibrator 37 may be directed to recalibrate the pressure sensor to a pressure range with lower values. Each of these changes would result in an assembly 10 which responds to lower pressures.

In another example, the processor 34 may decrease the time measurement period (e.g. to 5 minutes, 1 minute, etc.) and increase the measurement frequency (e.g. to 20 Hz, 100 Hz, etc.) if it detects that the integrated pressure is changing rapidly, which may indicate movement of the individual, justifying increasing the sensing frequency.

In another example, the assembly 10 may change measurement parameters of the pressure sensor 40 to increase the pressure threshold value, the alert value, or the measurement time period, or recalibrate the pressure range to a higher recalibrated pressure range, each of which allows less sensitive monitoring of pressure for healthier tissue. Where there is a prolonged period of low pressures and a lack of alert signals, the processor 34 may direct changes in measurement parameters to allow the assembly 10 to generate alert signals only with relatively high integrated pressures. Where the threshold pressure value is increased beyond the pressure range, the processor 34 directs the active calibrator 37 to recalibrate the pressure range to a higher recalibrated pressure range.

In another example, where the pressure readings are at the low end of the pressure range, the processor 34 may cause the active calibrator 37 to direct recalibration to a lower recalibrated pressure range. Similarly, where the pressure readings are at the high end of the pressure range, the processor 34 may cause the active calibrator 37 to direct recalibration to a higher recalibrated pressure range.

In another example, after an alert signal for turning the individual with the target surface, the active calibrator 37 recalibrates the pressure range to match the pressures being sensed after turning.

Output Device

The output device 50 is operably coupled to the processor 34 for receiving data from the processor 34. The output device 50 includes a communication element 52 which receives a signal corresponding to the comparative pressure, the alert signal, the first signal, the second signal, or a signal with other data, from the processor 34, for display and communication to the user. The communication element 52 is shown as including an LED bulb. The LED bulb communication element 52 can turn on or flash when the comparative pressure exceeds the threshold pressure value, when the alert signal is otherwise received, or on other conditions. Similarly, the communication element 52 could include a speaker or other suitable device which can communicate the above conditions.

Calibration of the Pressure Sensor

Calibration may be passive or active. With passive calibration, the pressure sensor 40 is calibrated to be operable within a certain pressure range, and the range remains constant. The circuit 70 provides passive calibration to pressure sensor 40. The adjustable sensor resistor 72 is permanently calibrated at the time of manufacture to operate in a selected range of pressures. For example, the adjustable sensor resistor 72 may operate in a pressure range varying from about 20 mm to about 30 mm Hg, from about 30 to about 40 mm Hg, from about 40 Hg to about 50 mm Hg, from about 50 mm to about 60 mm Hg, from about 60 mm Hg to about 70 mm Hg, or from about 70 mm Hg to about 80 mm Hg. In other cases, broader ranges may be applied (e.g. from about 35 mm Hg to about 50 mm Hg, from about 30 mm Hg to about 55 mm Hg, from about 30 mm Hg to about 60 mm Hg, or other ranges of about 25 or 30 mm Hg, etc.).

The electronic controlling element 30 includes an active calibrator 37 for calibrating the pressure sensor 40 to sense pressure within a selected pressure range. Active calibration allows changes to the pressure range within which the pressure sensor 40 senses pressure, facilitating measurement of substantial variations in the magnitude of the pressures sensed by the pressure sensor 40.

Active calibration facilitates accounting for variations in topical skin pressures on the target surface, which may vary considerably. For example, pressure exerted on a sole of a foot in an upright standing condition is substantially higher than pressure experienced on most surface areas of a torso in normal resting condition. Active calibration facilitates using the same pressure data acquisition assembly 10 on both surfaces. In addition, where the sensing portion 23 of the support web 20 includes multiple pressure sensors 40 (or multiple sensor elements 360 per FIG. 10 below), different pressures may be sensed at different portions of the sensing portion 23. Such local variations in pressure are particularly likely on relatively non-stationary areas of the skin (e.g. where portions of the skin cover joint areas, where due to movement temporal changes in pressure are experienced, etc.).

Using active calibration, the pressure range which is sensed by the pressure sensor 40 can be adjusted on an as-needed basis by the user, for example as part of the process of applying the support web 20, at defined time intervals (e.g. every 30 minutes, etc.), or when a change status occurs (i.e. when a change condition has been met).

Figure 5:
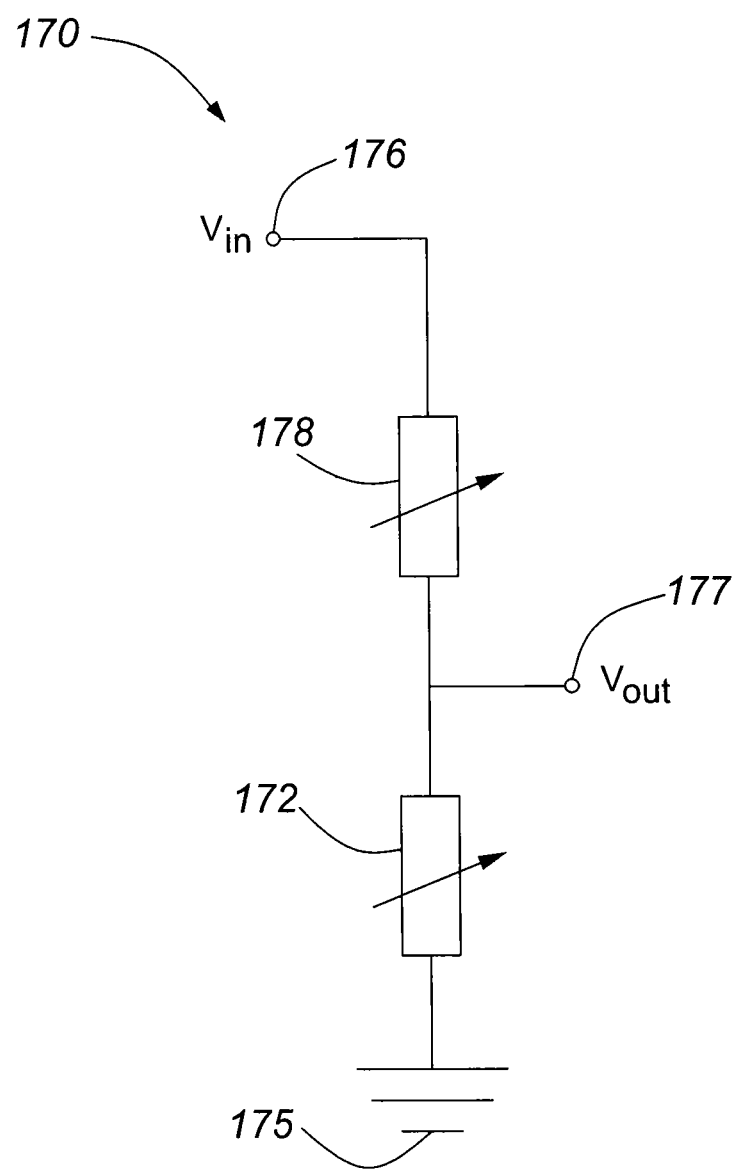
FIG. 5 is a schematic of an active calibration electrical circuit for use with the sensor of FIG. 1.

FIG. 5 is an electrical circuit 170 which provides active calibration and could be applied in the active calibrator 37. The electrical circuit 170 shares many features of the electrical circuit 70, and reference numerals in FIG. 5 including the same two digits as reference numerals in FIG. 3 have the same labels for those reference numerals. The voltage at $V_{out}$ 177 is defined by the adjustable sensor resistor 172, an adjustable calibration resistor 178, and the amperage of the current. Changing the resistance of the adjustable calibration resistor 178 adjusts the range of changes in resistance of the adjustable sensor resistor 172 which result in a detectable change in potential at $V_{out}$ 177. A user or the processor may set the resistance of the adjustable calibration resistor 178, thereby selecting the range in which the pressure is measured.

Figure 6:
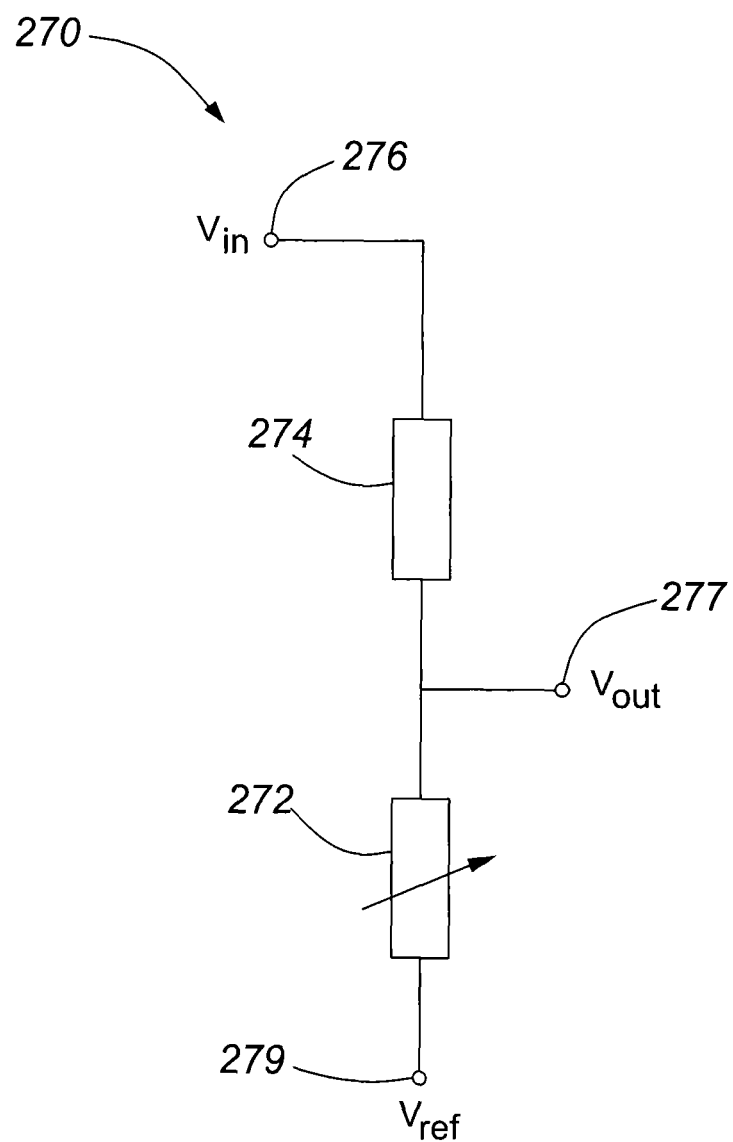
FIG. 6 is a schematic of an active calibration electrical circuit for use with the sensor of FIG. 1.

FIG. 6 is an electrical circuit 270 which provides active calibration and could be applied in the active calibrator 37. The electrical circuit 270 shares many features of the electrical circuit 70, and reference numerals in FIG. 6 including the same two digits as reference numerals in FIG. 3 have the same labels for those reference numerals. The voltage at $V_{out}$ 277 is defined by the adjustable sensor resistor 272, the constant resistor 274, the amperage of the current, and an applied reference voltage $V_{ref}$ 279. Changing the applied reference voltage $V_{ref}$ 279 adjusts the range of changes in resistance of the adjustable sensor resistor 272 which result in a detectable change in potential at $V_{out}$ 277. A user or the processor 34 may set the reference voltage $V_{ref}$ 279, thereby selecting the range in which the pressure is measured.

Each of the circuits 170, 270 allows selection of a pressure range in which the pressure is measured. The pressure is compared to the threshold pressure value to determine the comparative pressure, allowing pressure sensors with which the circuits 170, 270 are used to be applied to different pressure ranges.

Figure 8:
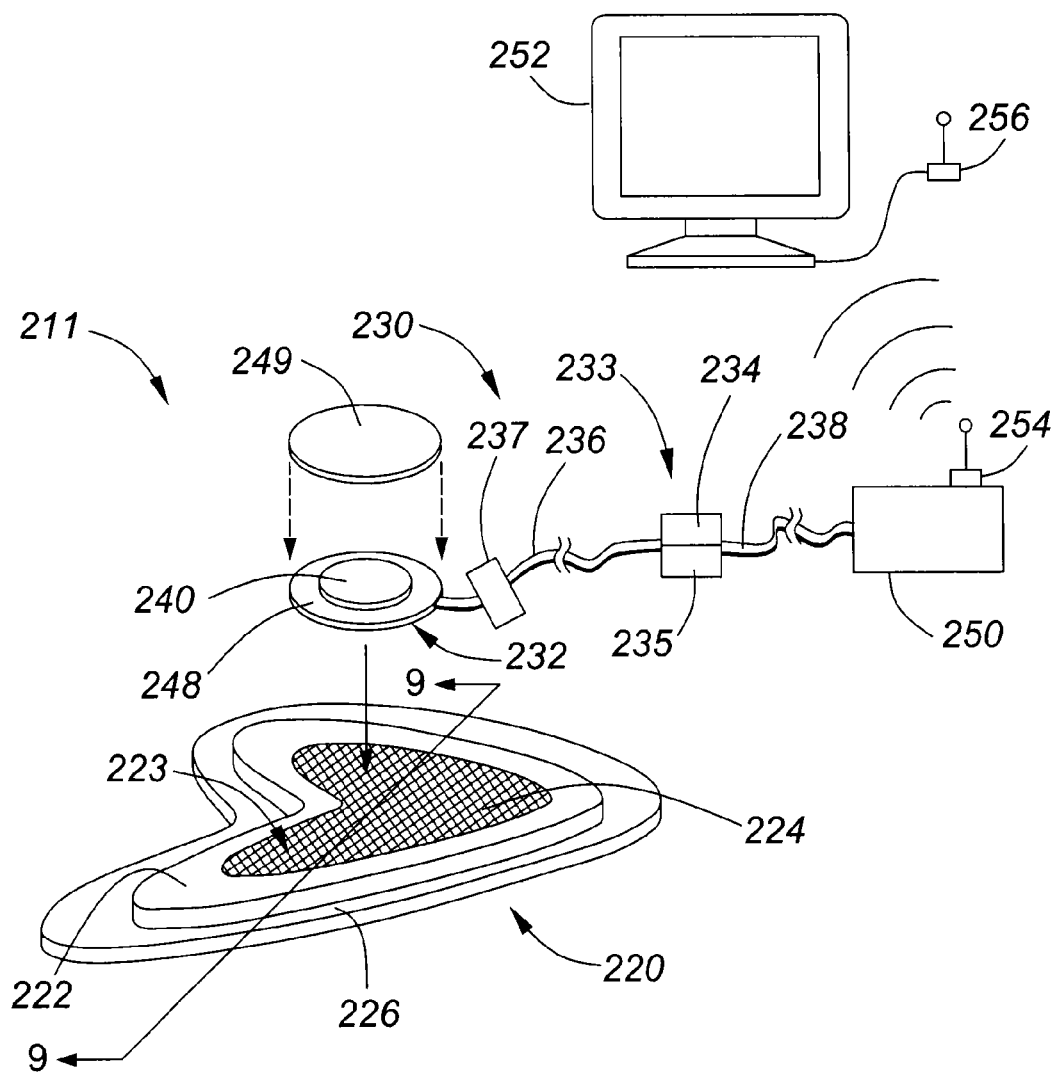
FIG. 8 is a perspective view of a bandage and pressure data acquisition assembly.

The active calibrator 37 is coupled to the pressure sensor 40 and may be housed or co-located in the processing element 33 with the processor 34 and computer readable medium 35 (as shown in FIG. 1), co-located with the pressure sensor 40, or located elsewhere (see calibrator 237 in FIG. 8). The active calibrator 37 facilitates use of the support web 20, upon calibration, on any or substantially any target surface of a user or animal, regardless of the conditions at the target surface at the target surface (e.g. joints or other moving tissue, bony prominences, etc.). The active calibrator 37 facilitates sensing pressure on target surfaces with substantial positional or temporal pressure variability (e.g. for use on target surfaces such as skin covering joints or other bony prominences, etc.).

The active calibrator 37 may be more suitable where reuse of the pressure data acquisition assembly 10, the electronic controlling portion 30, or the input element 34, is intended. In a disposable single-use pressure data acquisition assembly 10, the electronic controlling portion 30, or input element 34 may apply passive calibration only (i.e. having the circuit 70 as opposed to the circuits 170 or 270, and lacking the calibrator 37 as in the bandage and pressure data acquisition assembly 111 of FIG. 7). The support web 20 may be removable from the electronic controlling portion 30, sensor 40, and output device 50.

The pressure sensor 40 may be directed by the processor 34 to repeatedly and periodically measure pressure during a measurement time period (e.g. at least 1 minute, at least 5 minutes, at least 10 minutes, at least 15 minutes, at least 30 minutes, 15 minutes, etc.). The pressure sensor 40 may be directed by the processor 34 to, upon completion of a first series of measurements during a first time interval, initiate a second series of measurements during a second time interval. The initiation of the second series of measurements may occur automatically (e.g. on a regular basis, irregular basis, as a result of a condition being satisfied, etc.) or through manual initiation by a user. By leaving little or no time period between time intervals, the pressure data acquisition assembly 10 may continuously or substantially continuously monitor the target surface. The periodicity with which pressure is measured may be regular or irregular. The periodicity of the measurements may vary (e.g. between 0.5 Hz and 100 Hz, between 0.5 Hz and 25 Hz, etc.). Relatively high frequencies of pressure measurements (e.g. 100 Hz, etc.) facilitate regular and continuous monitoring where the target surface is mobile, for example if the bandage is being used for running injury prevention or on a diabetic foot ulcer. Lower frequencies may be applied where there is less movement, for example a bedridden patient. Higher frequencies are often used during calibration by the active calibrator 37 while the target surface is immobile to calibrate in a shorter period of time. During calibration, the processing element 33 may send a signal indicating that calibration is occurring to the output device 50 for display. The data obtained may be made available on a substantially real-time basis to a patient, physician, caregiver or other user, without requiring direct visual inspection of the surface area.

Bandage and Pressure Data Acquisition Assembly

Figure 7:
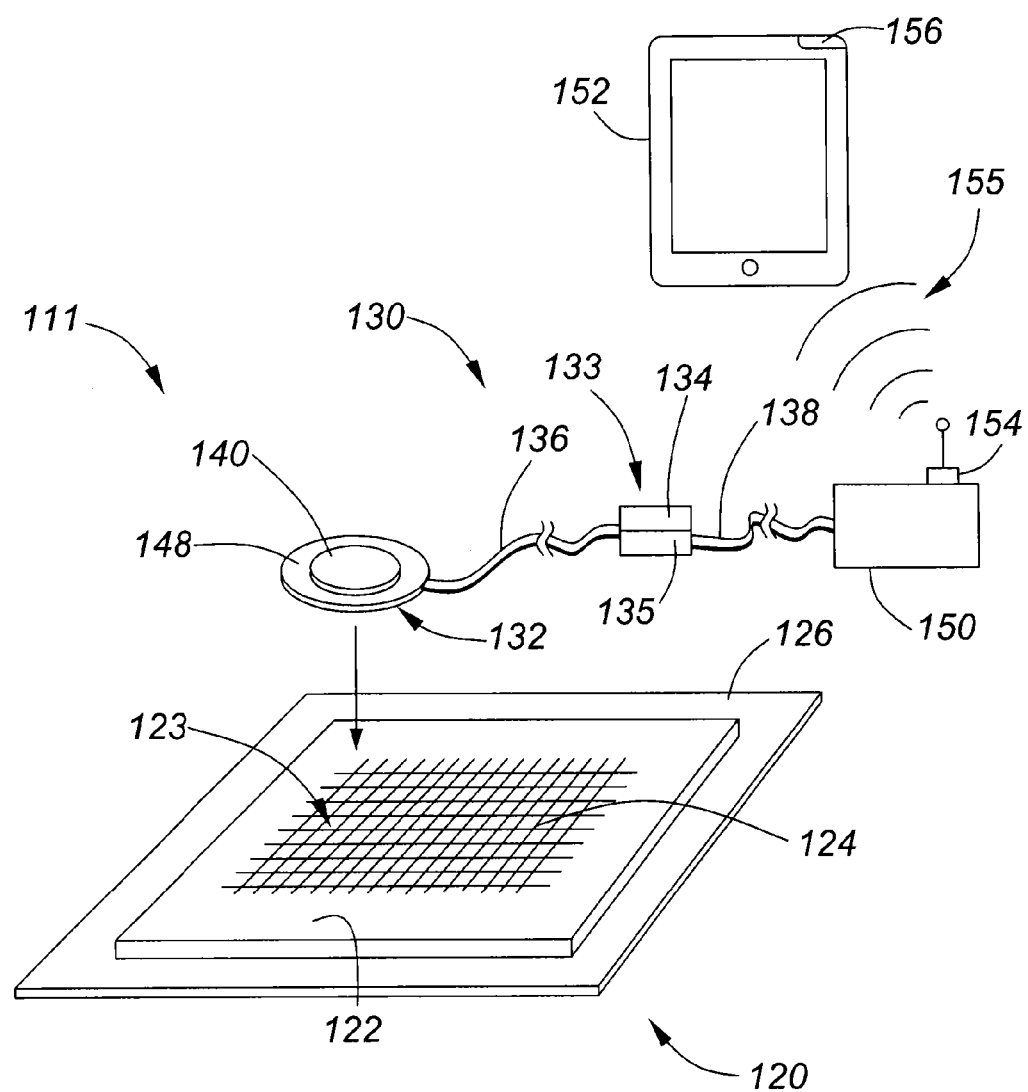
FIG. 7 is a perspective view of a bandage and pressure data acquisition assembly.

FIG. 7 shows a bandage and pressure data acquisition assembly 111. The bandage and pressure data acquisition assembly 111 shares many features of the data acquisition assembly 110, and reference numerals in FIG. 7 including the same two digits as reference numerals in FIG. 1 have the same labels for those reference numerals. The support web 120 is a bandage and includes the support portion 122, a treatment portion 124, and an adhesive portion 126. The support portion 122 provides a support substrate for the treatment portion 124. The treatment portion 124 overlaps with the sensing portion 123, with the treatment portion 124 being larger than the sensing portion 123 in the bandage 120.

The treatment portion 124 provides a suitable surface for contacting the target surface where the skin has compromised integrity or is otherwise sensitive. The treatment portion 124 may be prepared from a wide variety of materials, both natural and synthetic, that are compatible with such application. Suitable materials include one or more layers of a textile material, non-woven fabric, foam, fiber or fibrous materials, for example cotton, or biocompatible polymeric materials, such as polyethylene terepthalate, polypropylene, or blends of viscose rayon and polyolefins. The treatment portion 124 may be constructed from one or more layers of fiber gauze or other materials for providing cushioning and absorbing wound exudates.

The adhesive portion 126 includes an adhesive for adhering and securing the bandage 120 to the target surface in a manner that substantially follows the contours of the user and substantially conforms to the surface of the skin at the target surface. The adhesive may be a glue, glue-like substance, pressure acrylic adhesive or any other material. The adhesive portion 126 substantially conforms to the target surface and adheres the treatment portion 124 to the target surface. The support web 20, or other embodiments lacking the adhesive portion 126, may be secured to the target surface by tape or other means that are separate from the support web 20.

Peripheral Communication Element

The output device 150 includes a first output module 154 which communicates a signal corresponding to the comparative pressures value received from the processor 134 to a second output module 156. The second output module 156 receives the comparative pressure from the first output module 156 for display on a communication element 152. The communication element 152 is shown as including a screen on a tablet. Similarly the communication element 152 could be a screen on a different device or any suitable display, for example as described above. Communication between the first output module 154 and the second communication module 156 is shown as being through a wireless connection 155, but any suitable connection can be used.

The second output module 156 and the communication element 152 are positioned peripherally to the bandage 120. The processor 134, the computer readable memory 135, and active calibrator 137 may conveniently be assembled and co-housed with the sensor 140 or with the first output module 154. The processor 134, computer readable memory 135, and active calibrator 137 may be co-located with the bandage 120 or located peripherally to the bandage 120.

The communication element 152 displays the comparative pressure or derivatives thereof (e.g. the fraction of the plurality of measured pressure values that exceeds the threshold pressure, etc.). The output device 150 may include any suitable device for displaying the comparative pressure (e.g. a TV screen, LCD, LED backlit screen, a computer screen, a tablet screen, a smartphone screen, a three-dimensional display, a printer, a USB key or other electronic storage device, etc.). The output device 50 may display the comparative pressure in different ways (e.g. auditory, numerically, graphically, etc.). Graphical displays may include various graphs (e.g. pie-chart, bar graph, a graphical representation of the target area, etc.).

Pressure Sensors with Protective Covering

Figure 9:
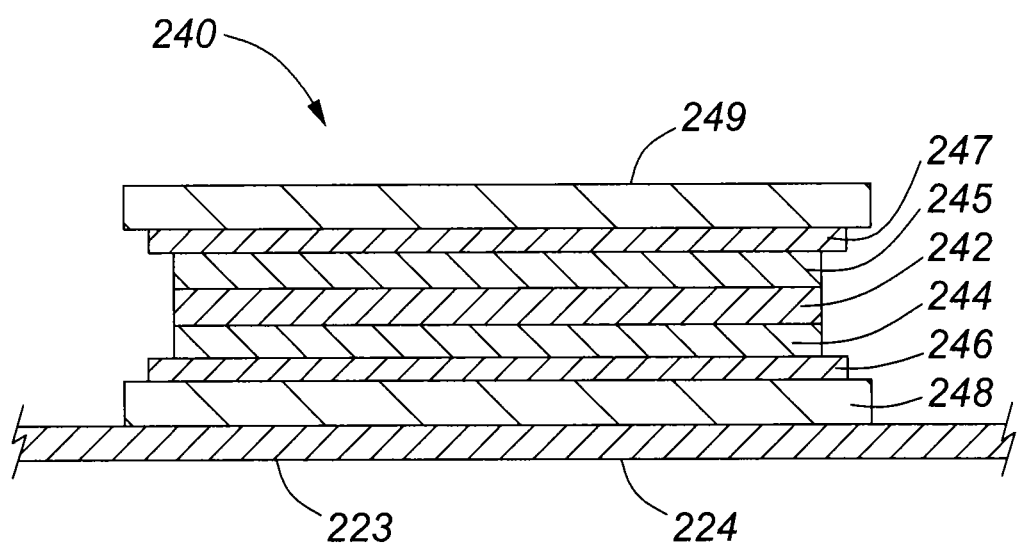
FIG. 9 is a cross-sectional view along of a sensor of the pressure data acquisition assembly of FIG. 8 along plane 9-9.

FIGS. 8 and 9 show an alternative bandage and pressure data acquisition assembly 211. The bandage and pressure data acquisition assembly 211 shares many features of the data acquisition assembly 110, and reference numerals in FIGS. 8 and 9 including the same two digits as reference numerals in FIGS. 1 and 2 have the same labels for those reference numerals. The bandage 220 has a heart shape, including at the supportive portion 222, sensing portion 223, treatment portion 224, and adhesive portion 226. In addition to the heart shape of the bandage 220 and the substantially rectangular shapes of the support web 20 and bandage 120 (see FIGS. 1 and 7), any suitable shape may be applied (e.g., oval-shaped, heart-shaped. etc.).

The sensor 240 includes a protective second substrate carrier layer 249 externally to the second flexible surface layer 247. The second substrate carrier layer 249 provides resistance to abrasion of the sensor 240 by protecting the second flexible surface layer 247. The second substrate carrier layer 249 may be made from the same material as the first substrate carrier layer 248 (e.g. PET, etc.) or of a different material. The second substrate carrier layer 248 would be prepared from a material selected to protect (e.g.

from delamination, etc.) and be compatible with the second flexible surface layer 247, but unlike the first substrate carrier layer 248, need not be compatible with the sensing portion 223 and treatment area 224. The second substrate carrier layer 249 may also be selected to maintain the correct durometer, elasticity, and resilience in the face of pressures and temperature changes. This mitigates the potential for higher or prolonged pressures, or increased temperatures, to affect calibration of the pressure sensor 240.

Multiple Sensor Elements

Figure 10:
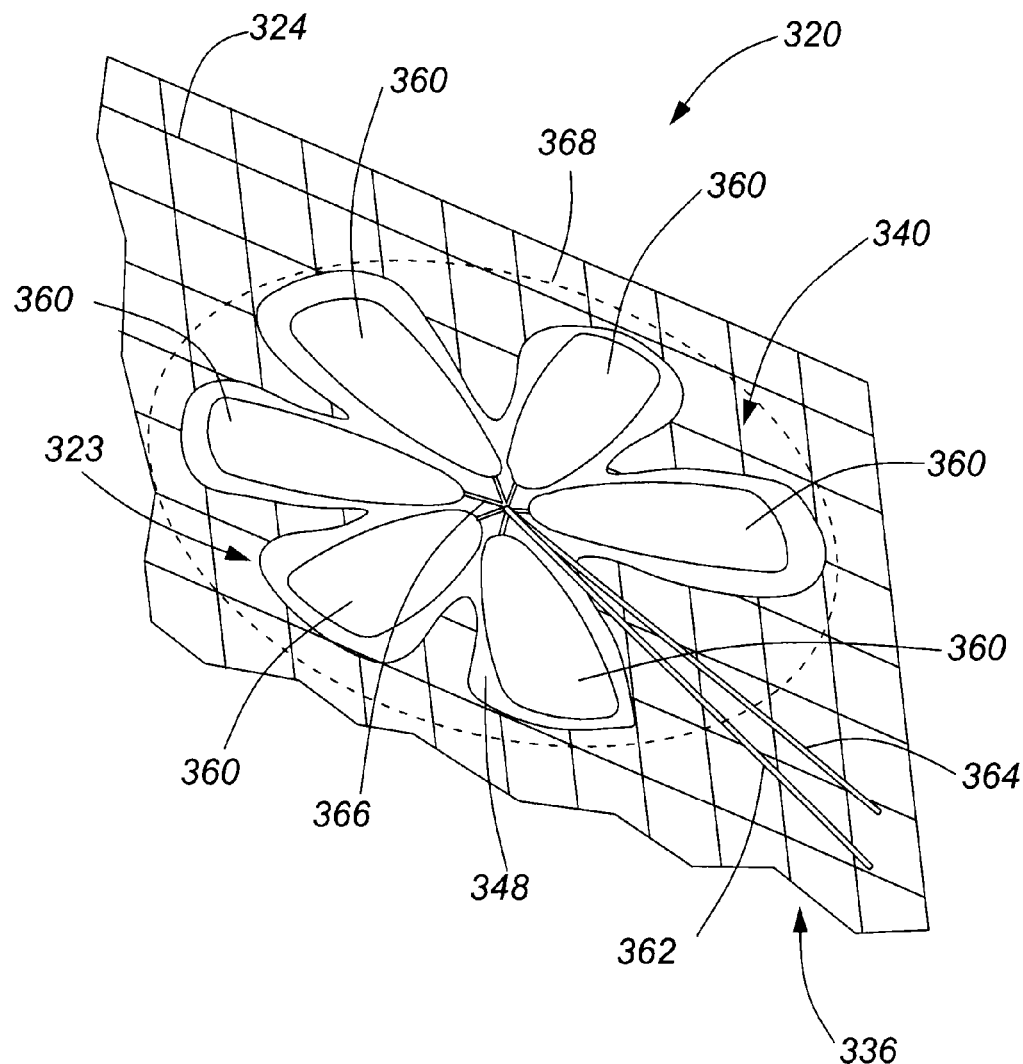
FIG. 10 is a perspective view of a sensor for a pressure data acquisition assembly.

FIG. 10 shows the sensing portion 323 of a support web 320. The pressure sensor 340 includes six circumferentially positioned lobe-shaped sensor elements 360 connected to the sensor support layer 348. The sensor support layer 348 is connected to the treatment portion 324. The first connection 336 includes electrical leads 362 and 364 for respectively providing input to and receiving output from the pressure sensor elements 360. The electrical lead 362 provides power to the pressure sensor elements 360 and the electrical lead 364 receives signals corresponding to changes in pressure on the sensor elements 360 (e.g. a change in voltage across a circuit where the pressure sensor elements 360 include a piezoresistive material, etc.). Electrical leads 368 connect the sensor elements 360 to the electrical leads 362 and 364. Where the pressure sensor elements 360 are circumferentially spaced, a circumference 368 is defined around the pressure sensor 340.

For example, each sensor element 360 may generate a separate signal for transmission of individual pressure measurements, or only the sensor element 360 with the greatest signal strength at a given time point will send a transmission, etc.

The sensor 340 includes six lobe-shaped sensor elements 360. Alternatively, sensor elements may have other shapes and may be present in other numbers (e.g. 3, 4, 5, 6, 7, 8, 9, or 10 sensor elements, etc.).

Plurality of Sensors

Figure 11:
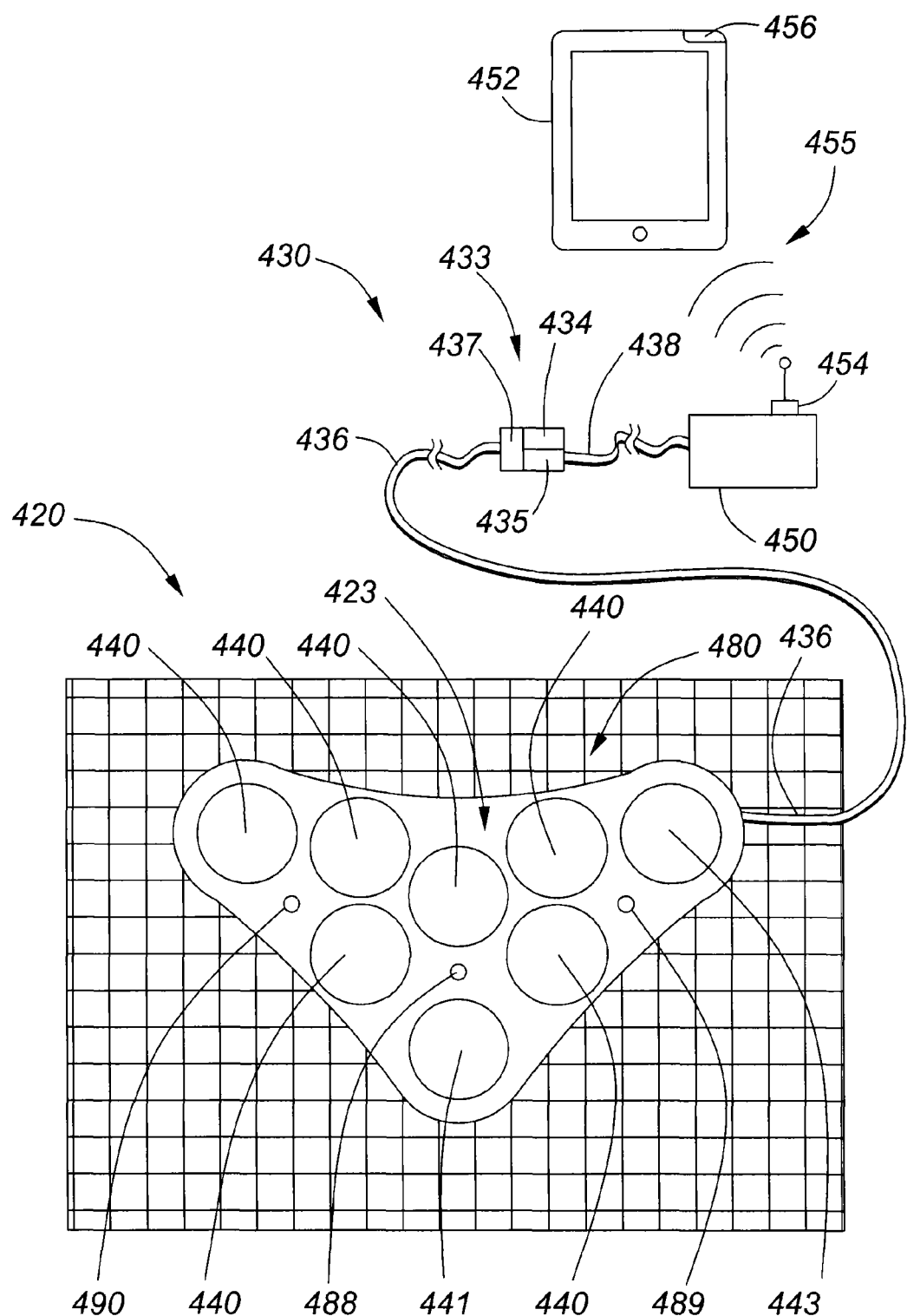
FIG. 11 is a perspective view of a pressure data acquisition assembly.

FIG. 11 shows a pressure data acquisition assembly 410 wherein the support web 420 includes a sensor array 480 shaped for adhering to a sacrum. The pressure data acquisition assembly 410 shares many features of the data acquisition assembly 10, and reference numerals in FIG. 11 including the same two digits as reference numerals in FIG. 1 have the same labels for those reference numerals. The sensor array 480 includes eight sensors 440 arranged for application to a sacral area of a user, although other sensor arrays could be prepared with two or more sensors (e.g. 3, 4, 5, 6, 7, 8, 9, 10, etc.). The sensors 440 may be substantially identical in shape, size and electronic configuration, or individual sensors 440 may have a different shape, size or electronic configuration.

The sensor array 480 may facilitate treatment or prevention of pressure-based injuries on non-planar or irregular surfaces compared to use of a support web having only one sensor (e.g. the support web 20, or bandages 120, 220 of FIGS. 1, 7, and 8), for example target surfaces comprising a bony protrusion, where due to the non-planar or irregular shape of the target surface, different portions of the target surface areas are subject to different pressures. The support web 420 is flexible and conforms to the target area. The sensors 440 in the array 480 are shown as sharing a common first substrate carrier layer 448. The sensors in the array 480 may alternatively have individual first substrate carrier layers which do not overlap (not shown).

The individual sensors 440 may be calibrated to the same measured pressure range or different ranges. The processor 434 may be configured to apply signals from all different pressure sensors 440 to the output shown by the output device 450 equally. Alternatively, the processor 434 may be configured to apply signals from different pressure sensors 440 to the output shown by the output device 450 differently. For example, the processor 434 may be configured to provide the alert signal when 50% of the measured input parameters measured by a first pressure sensor 441 exceed the alert value, or when 75% of the measured input parameter measured by a second pressure sensor 443 exceeds the threshold pressure value. For example, the first and second pressure sensors 441, 443 could have different threshold pressure values assigned to them.

In another example, where the processor directs the calibrator 437 to recalibrate the first pressure sensor 441 to a recalibrated pressure range, the processor 434 may confirm that both the first pressure sensor 441 and the second pressure sensor 443 are experiencing similar pressure readings. If this is confirmed, the first pressure sensor 441 will be recalibrated. If not, the processor will interpret this as a malfunction (e.g. due to the first or second pressure sensors 441, 443 becoming detached form the individual, etc.) and send an alert signal. In this example, the second pressure sensor 443 would be located on the individual outside of the target surface. In this example, the second pressure sensor 443 may be excluded from the grouping algorithm (see below) and used only as a reference for the first pressure sensor 441 and other pressure sensors 440.

The processor 434 may be configured in such a manner that data acquired from each individual pressure sensor 440 is provided to the output device 450, so that individual pressure sensors 440 can be tracked on the output device 450.

The processor 434 and output device 450 may represent data of one or more pressure sensors 440 grouped in accordance with a grouping algorithm. The grouping algorithm may be applied by the processor 434 and then provided to the output device 450, or may be applied by the output device 450. In the grouping algorithm, the data from each pressure sensor 440 may be treated equally, or a varying weighting may be applied to each data set depending on which sensor the data is acquired from (e.g. as described above with respect to the first and second pressure sensors 441, 443 having different threshold pressure values or different percentages of measurements above the threshold pressure value to trigger an alert, etc.).

The calibrator 437 is in communication with the pressure sensors 440 to calibrate some or all of the pressure sensors 440. The calibrator 437 may calibrate the pressure sensors 440 together, in groups, or individually. The calibrator 437 may calibrate the pressure sensors 440 with different pressure ranges or the substantially similar pressure ranges. The calibrator 437 may include several individual calibrators (not shown), each for one or more of the pressure sensors 440.

The calibrator 437 and the pressure sensors 440 may be in communication with each other to direct calibration throughout the sensor array 480. For example, the first pressure sensor 441 may be calibrated to a pressure range applicable to the second pressure sensor 443, or to all other pressure sensors 440. The first pressure sensor 441 may be directed by the processor 434 to recalibrate the second pressure sensor 443, or all the pressure sensors 440, at a recalibration frequency (e.g. every 30 minutes) or upon a change status occurring.

In another example, where an alert value is detected at the first pressure sensor 441, the alert value of the second pressure sensor 443 may change. The first and second pressure sensors 441, 443 may be controlled by the same electronic control element 430 as shown or by different electronic control elements (not shown).

Where more than one pressure sensor array 480 is used, communication between pressure sensor array 480 may have an analogous relationship where a first pressure sensor array 480 calibrates a second pressure sensor cluster 480 (not shown).

Display of Target Area by Output Device

Figure 12:
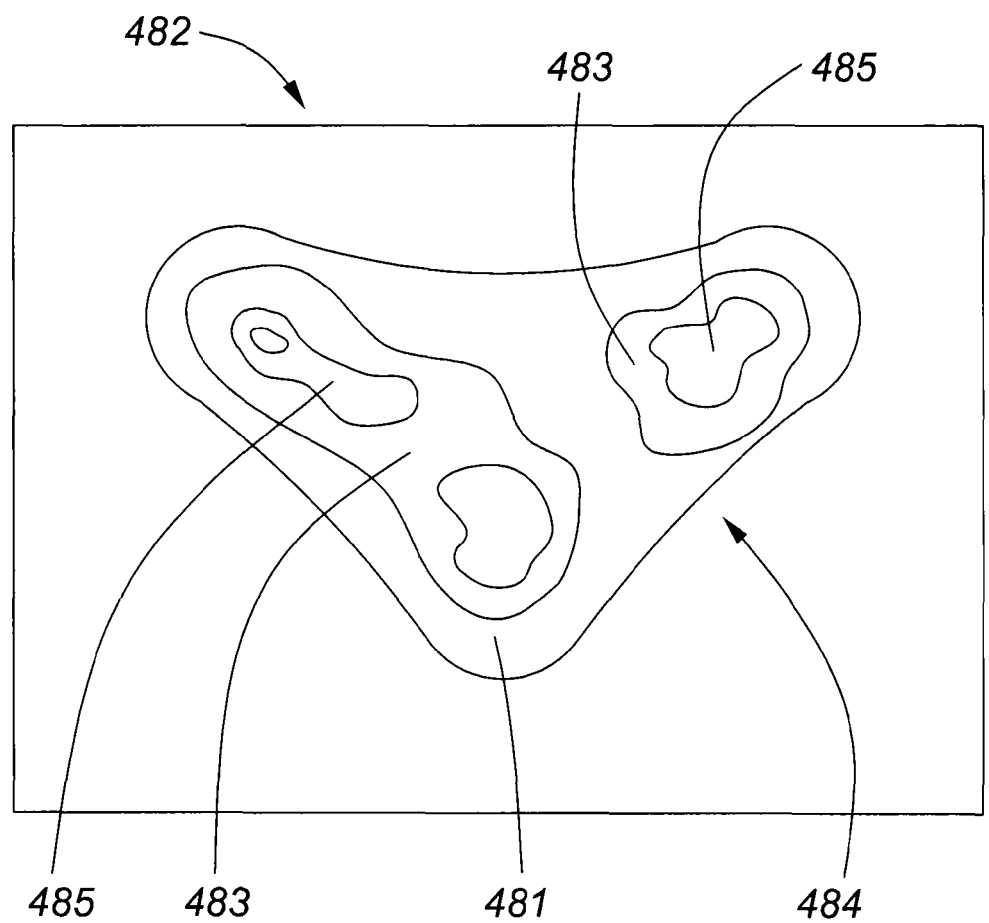
FIG. 12 is a schematic of a graphical display of data sensed by the pressure data acquisition assembly of FIG. 11.

FIG. 12 is a schematic of a graphical display 482 on the communication element 452. In the graphical display 482, a target area 484 of the sensor array 480 corresponding to an individual's sacrum is displayed schematically. Portions of the target area in relation to which signals of different integrated pressures are being displayed by the output device 450 are shown with a color coded scheme. For example, a first color 481 if less than 25% of the comparative pressures exceed the alert value during the measurement time period, a second color 483 if between 25% and 50% of the comparative pressures exceed the alert value during the measurement time period, and a third color 485 for the alert status where more than 90% of the comparative pressures exceed the alert value. The third color 485, may be emphasized (e.g. by flashing, repetitive changes in color during display, etc.).

In another example, the processor 434 may cause the communication element 452 to display a graphical representation of the target surface and integrated pressures with the first color 481 if less than 35% of the comparative pressures exceed the alert value during the measurement time period, the second color 483 if between about 35% and 90% of the comparative pressures exceed the alert value during the measurement time period, and the third color 485 if more than about 90% of the comparative pressures exceed the alert value during the measurement time period.

In another example, the comparative pressures may also be displayed, directly or indirectly, with each of the colors 481, 483, and 485 is displayed to reflect different comparative pressures (not shown).

The graphical display 482 can be used to assess progress of wound healing and to provide diagnostic information helpful to decisions as to patient adjustment, turning regimens, and other applications.

Measurement of Other Biological Parameters

The sensor array 480 includes a first biological parameter sensor 488 and a second biological parameter sensor 489, each for sensing a value of a biological parameter on the sensing surface 423. Biological parameters are features at the target surface other than pressure which are relevant to diagnostic or other useful information, or which affect performance of the pressure sensors 440. Biological parameters include, for example, temperature, pH, bacterial load, or humidity of the target surface, and muscle activity (e.g. measured through electromyography, etc.), etc. Data of biological parameters may be integrated over time and compared to a biological parameter alert value or biological parameter change condition.

The first and second biological parameter sensors 488, 489 sense biological parameters on different areas of the sensing surface 423. The first and second biological parameter sensors 488, 489 may sense the same biological parameters or different biological parameters.

The computer readable memory 435 may be configured to store threshold biological parameter values, and the processor 434 may be configured to calculate comparative biological parameter values based on threshold biological parameter values. The biological parameter sensors 488, 489 may include variable resistance circuits similarly to the electric circuit 70, and the active calibrator 437 may set a range within which biological parameters are measured through circuits similar to the electrical circuits 170, 270. However, some biological parameters in some cases display absolute values which may not benefit from active calibration (e.g. temperature, moisture, etc.). The output device 450 may communicate comparative biological parameter values based on first, second, or alert signals similarly to the corresponding signals for comparative pressures.

In addition to being reported by the output device 450, the biological parameter values may affect how the processor 434 processes the comparative pressures and integrated pressures, may direct the processor 434 to reapply the calibrator 437 to some or all of the pressure sensors 440 for recalibration, alter the first, second, or alert values of one of more of the sensors 440, or otherwise affect sensing, processing, or display of data.

For example, at higher temperatures, the first, second, or alert values may be shifted to lower integrated pressures.

In another example, where the temperature does not decrease over time (e.g. at a sufficient rate per hour, etc.), this may be an indicator of poor wound healing, which could result from excessive pressure on the wound, and suggest that the individual on whom the support web 420 is placed turn more frequently or change position, or that the first, second, or alert values be lowered for some or all sensors 440.

In another example, integrated temperature values above the applicable change condition result in the processor 434 activating the calibrator 437 to recalibrate the pressure range of some or all of the pressure sensors 440, and change the pressure threshold values and alert values, as the materials the support web 420 is made from may be affected by the heat.

In another example, a spike in integrated temperature values suggests that active healing is occurring at the target surface and the threshold pressure values, alert values, and measurement time periods are all decreased. This provides milder, lower pressure conditions for the healing to continue.

In another example, pH may be an indicator of bacterial load, which may delay or otherwise impede healing of a wound. The effect of moisture is context dependent, with high moisture in some circumstances promoting epithelial cell migration and healing, and in other circumstances, impeding healing. A user would be able to select which relationship between moisture and the measurement parameters applies in this case. Muscle activity, which may be measured by electromyography or other methods, provides information related to where and how much movement has been occurring on the target surface. These and other biological parameters measured at the target surface, and whether or how often selected comparative values of the biological parameters have been exceeded, may be useful diagnostic information, in addition to triggering biological parameter change conditions.

Feedback Element

The support web 420 includes a feedback element 490 in communication with the processor 434. The processor 434 may direct the feedback element 490 to take an action with respect to the individual on whom the target surface is located. The action may be directed to reduce pressure or otherwise improve conditions at the target surface, or provide sensing data otherwise useful for diagnosis. The action may be taken in response to an alert status or change status (based on pressure data or biological parameter data). The feedback elements may for example provide vibration, heat, transcutaneous electrical nerve stimulation or other muscle stimulation, modification of moisture levels, inflation of air bladder pockets, administration of antibiotics or other drugs, or other stimulus or action. Similarly, where the sensor array 480, electronic controlling element 430, and output element 450 are incorporated into a bed or mattress, the feedback element may decrease or increase pressure in the bed by deflating or inflating air pockets, or may signal the individual in the bed (and on whom the target surface is located) to do the same through a manual control.

Resistance Range Biasing Circuit

Figure 13:
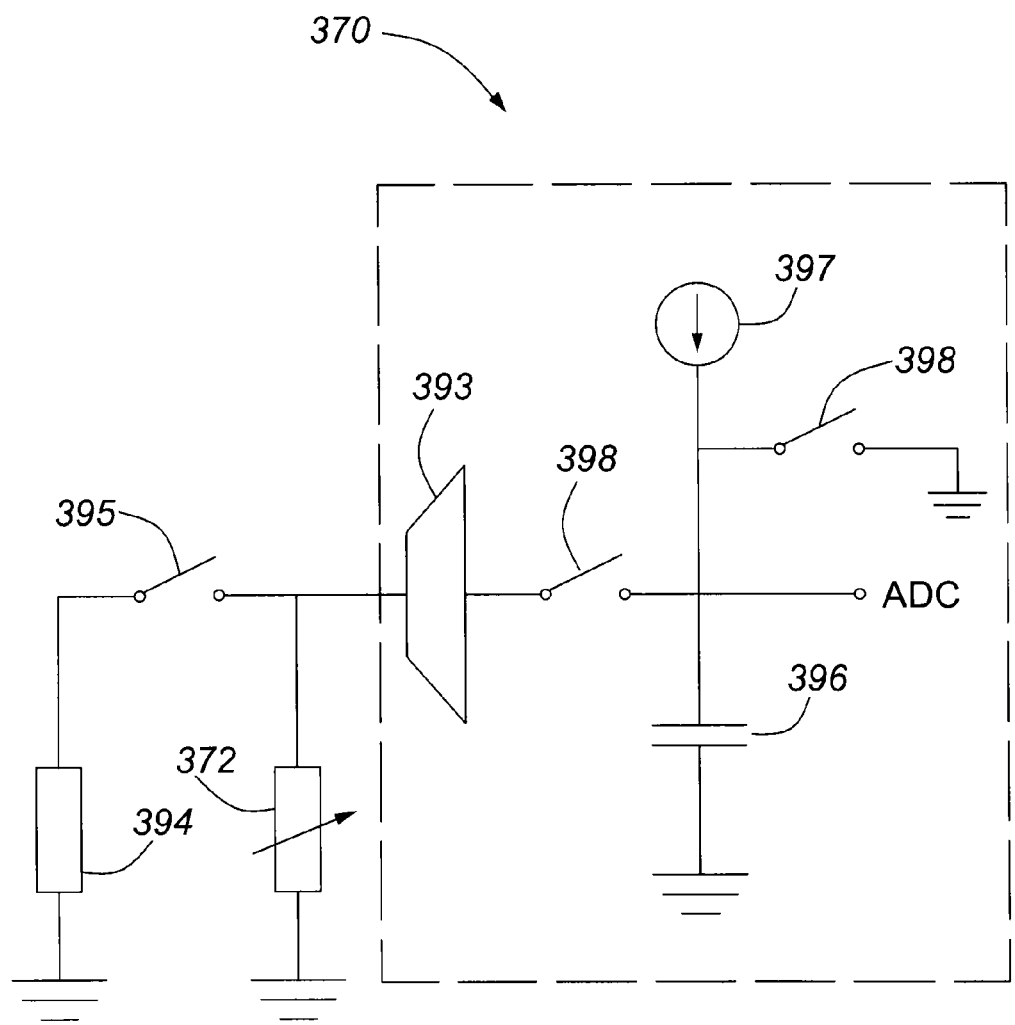
FIG. 13 is a schematic of an electrical drain circuit for use with the sensor of FIG. 1.

FIG. 13 is an electrical drain circuit 371 including a current time measurement unit 392 for use with the pressure sensors 40, 140, 240, 340, and 440 or biological parameter sensors 488, 489. The electrical drain circuit 371 shares many features of the electrical circuit 70, and reference numerals in FIG. 13 including the same two digits as reference numerals in FIG. 3 have the same labels for those reference numerals. The current time measurement unit 392 facilitates sensing pressure values over a greater range. The current time measurement unit 392 includes a low resistance resistor 394 connected in series to the adjustable sensor resistor 372 by a switch 395. Where the adjustable sensor resistor 372 is operating at the upper end of its resistance range, measurements received by the pressure or other biological parameter sensor the electrical drain circuit 371 is operating with may have a drop in frequency. To maintain a selected frequency of measurement, the switch 395 will close, lowering the overall impedance of the electrical drain circuit 371 by including the low resistance resistor 394 in the circuit. The processor with which the electrical drain circuit 371 is used (e.g. processors 34, 134, 234, or 434, etc.) would include algorithms for normalizing the pressure or other biological parameter values to account for the lower resistance. The processor may also change the threshold pressure value or other biological parameter value in response to the switch 395 closing. In some examples, the switch 395 would be absent and the low impedance resistor 394 permanently included in a circuit to increase the frequency of pressure value measurements to bias for certain measurement ranges (e.g. where high resistance values are expected in the circuit, etc.).

The current time measurement unit 392 includes a reference capacitor 396 to provide a charging time reference to the current time measurement unit 392. The charging time reference is used by the current time measurement unit 392 as a comparator. An adjustable current source 397 and drain switches 398, 399 are also in the current time measurement unit 392 to drain current from the circuit 370 before closing the switch 395 to bias the resistance range of the adjustable sensor resistor 372. The current time measurement unit 392 also includes a multiplexer 393 for allowing multiple pressure or biological parameter sensors to be in communication with the current time measurement unit 392. The current time measurement unit 392 itself may direct draining the circuit 370 and closing the switch 395, or the processor may direct the current time measurement unit 392 to operate these functions.

Use of the Pressure Data Acquisition Assembly

The support web 20 may be used to apply to one or more external target surface on the body, including skin that is wounded, injured, or prone to injury, etc. Thus, the present disclosure includes a method employing the pressure data acquisition assembly 10 for treating or preventing injury of an external surface area of a human body. Thus the present disclosure includes use of the pressure data acquisition assembly 10 in the treatment or prevention of injury to an external surface area of the body.

The pressure data acquisition assembly 10 facilitates monitoring of individuals whose peripheral sensory perception is compromised. Such patients experience, or are prone to experience, unchecked pressure, which may lead to complications including focal ischemia, venous injury, pressure necrosis, ulceration, and in the worst cases, infection and gangrene. Through use of the pressure data acquisition assembly 10, such injuries may be mitigated, prevented, or treated. In addition, the pressure data acquisition assembly 10 may facilitate the treatment of patients lacking normal mobility (e.g. bedbound patients, wheelchair patients, sedated patients, amputees, etc.). The pressure data acquisition assembly 10 may be used both for inpatient and outpatient care. Patients that may include diabetic patients, and patients suffering from ulcers (e.g. decubitus ulcers, etc.). The pressure data acquisition assembly 10 may facilitate prevention of injury (primary prevention), mitigation of injury recurrence (secondary prevention), and/or treatment of a wound or injury (tertiary prevention).

The data acquired using the pressure data acquisition assembly 10 may be used by the patient, a physician, medical personnel, caregiver or any other user to prevent injury to the skin or underlying tissue, take corrective action or treat an injury or wounded portion of the body.

Application of the bandage and pressure data acquisition assembly 111 to the target surface is facilitated by the adhesive portion 126 of the bandage 120, which is arranged to adhere the bandage 120 to the external surface area of the body (e.g. the scalp, sacrum, scapula, elbows, knees, greater trochanter, ischial tuberosity, include lower and upper extremity stumps in amputees, etc.).

Examples Only

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disc read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

At least some of the elements of the various electronic controlling elements described herein are implemented via software and may be written in a high-level procedural language such as object oriented programming or a scripting language. Accordingly, the program code may be written in C, C++ or any other suitable programming language and may comprise modules or classes, as is known to those skilled in object oriented programming. Alternatively, at least some of the elements of the various electronic controlling described herein that are implemented via software may be written in assembly language, machine language or firmware. In either case, the program code can be stored on a storage media or on a computer readable medium that is readable by a general or special purpose electronic device having a processor, an operating system and the associated hardware and software that implements the functionality of at least one of the embodiments described herein. The program code, when read by the electronic device, configures the electronic device to operate in a specific and defined manner in order to perform at least one of the methods described herein.

The methods described herein include methods are capable of being distributed in a computer program product comprising a transitory or non-transitory computer readable medium that bears computer usable instructions for one or more processors. The medium may be provided in various forms such as one or more diskettes, compact disks, tapes, chips, USB keys, external hard drives, wire-line transmissions, satellite transmissions, internet transmissions or downloads, magnetic and electronic storage media, digital and analog signals, tablet or smartphone apps, and the like. The computer useable instructions may also be in various forms, including compiled and non-compiled code.

The above-described embodiments are intended to be examples only. Alterations, modifications and variations can be effected to the particular embodiments by those of skill in the art without departing from the scope, which is defined solely by the claims appended hereto.

What is claimed is:

1. A pressure data acquisition assembly comprising:
a support web for applying to a target surface of a body of an individual;
a first pressure sensor connected to the support web for sensing at a first frequency a first pressure applied to the target surface;
a calibrator in operative communication with the first pressure sensor for calibrating the first pressure sensor to a first pressure range within which the first pressure sensor senses the first pressure;
a processing element in operative communication with the first pressure sensor for receiving first pressure signals corresponding to values of the first pressure from the first pressure sensor at the first frequency, and with the calibrator for recalibrating the first pressure sensor, the processing element comprising:
a computer readable memory for storing measurement parameters comprising a first threshold value corresponding to a first threshold pressure, a first measurement time period, a first alert value, and a first change condition; and
a processor in operative communication with the computer readable memory for accessing the measurement parameters, comparing the first pressure to the first threshold pressure to provide a first comparative pressure, integrating the first comparative pressure over the first time measurement period to provide a first integrated pressure, comparing the first integrated pressure with the first alert value to determine a first alert status, comparing the first integrated pressure with the first change condition to determine a first change status, and changing at least one measurement parameter or recalibrating the first pressure sensor to a first recalibrated pressure range, according to the first change status; and
an output device in communication with the processing element for receiving signals comprising data from the processing element and displaying the data.

2. The assembly of claim 1 further comprising a second pressure sensor for sensing at a second frequency a second pressure applied to the target surface;
wherein the calibrator is further in operative communication with the second pressure sensor for calibrating the second pressure sensor;
the processing element is in operative communication with the second pressure sensor for receiving second pressure signals corresponding to values of the second pressure from the second pressure sensor at the second frequency, and with the calibrator for recalibrating the second pressure sensor;
the measurement parameters further comprise a second threshold value corresponding to a second threshold pressure, a second measurement time period, a second alert value, and a second change condition;
the processing element is further for comparing the second normalized pressure to a second threshold pressure value to determine a second comparative pressure;
the processor is in operative communication with the computer readable memory for accessing the measurement parameters, comparing the second pressure to the second threshold pressure to provide a second comparative pressure, integrating the second comparative pressure with time over the second time measurement period to provide a second integrated pressure, comparing the second integrated pressure with the second alert value to determine a second alert status, comparing the second integrated pressure with the second change condition to determine a second change status, and changing at least one measurement parameter or recalibrating at least one of the first pressure sensor to a first recalibrated pressure range and the second pressure sensor to a second recalibrated pressure range, according to the second change status.

3. The assembly of claim 2 wherein the data comprises data of the first and second comparative pressures and the relative locations of the first and second pressure sensors on the target area, and the data is displayed visually.

4. The assembly of claim 2 wherein the first frequency and the second frequency are substantially equal.

5. The assembly of claim 2 wherein the first pressure range and the second pressure range are substantially equal.

6. The assembly of claim 2 wherein the calibrator is for calibrating the first pressure sensor and the second pressure sensor with a single input action.

7. The assembly of claim 2 wherein the first recalibration pressure range and the second recalibration pressure range are substantially equal.

8. The assembly of claim 2 wherein the first threshold pressure and the second threshold pressure are substantially equal.

9. The assembly of claim 1 further comprising a biological parameter sensor connected to the support web for sensing at a biological parameter frequency a biological parameter of the target surface;
wherein:
the processing element is in operative communication with the biological parameter sensor for receiving biological parameter signals in a biological parameter value range corresponding to biological parameter values at the biological parameter frequency;

the measurement parameters further comprise a biological threshold value corresponding to a threshold biological parameter value, a biological parameter measurement time period, a biological parameter alert value, and a biological parameter change condition; and the processor is in operative communication with the computer readable memory for accessing the measurement parameters, comparing the biological parameter values to the threshold biological parameter value to provide a comparative biological parameter value, integrating the comparative biological parameter value over the biological parameter time measurement period to provide an integrated biological parameter value, comparing the biological parameter value with the biological parameter alert value to determine a biological parameter alert status, comparing the biological parameter integrated pressure with the biological parameter change condition to determine a biological parameter change status, and changing at least one measurement parameter or recalibrating the first pressure sensor to the first recalibrated pressure range, according to the biological parameter change status; and the output device is in communication with the processing element for displaying the comparative biological parameter value.

10. The assembly of claim 9 wherein the processing element is in operative communication with the calibrator for recalibrating the biological parameter sensor to a recalibrated biological parameter range according to the biological parameter change status.

11. The assembly of claim 9 further comprising a feedback element connected to the support web for performing an action on the target surface for performing the action in response to the biological parameter alert status.

12. The assembly of claim 1 further comprising a feedback element connected to the support web for performing an action on the target surface for performing the action in response to the first alert status.

13. The assembly of claim 1 wherein the support web comprises a treatment portion for contacting sensitive skin.

14. The assembly of claim 1 wherein the support web comprises an adhesive material for adhering the support web to the target surface.

15. A method of acquiring pressure data comprising:
applying a first pressure sensor to a target surface of a body of an individual;
sensing by the first pressure sensor at a first frequency, a first pressure applied to the target surface;
calibrating, by a calibrator, the first pressure sensor to a first pressure range within which the first pressure sensor senses the first pressure;
providing first measurement parameters comprising a first threshold value corresponding to a first threshold pressure, a first measurement time period, a first alert value, and a first change condition;
comparing by a processor, the first pressure to the first threshold pressure to provide a first comparative pressure;
integrating, by the processor, the first comparative pressure over the first time measurement period to provide a first integrated pressure;
comparing, by the processor, the first integrated pressure with the first alert value to determine a first alert status;
comparing, by the processor, the first integrated pressure with the first change condition to determine a first change status;
changing, by the processor, at least one measurement parameter or recalibrating the first pressure range to the first recalibrated pressure range, according to the first change status; and
displaying, at an output device, at least one of the first integrated pressure, the first alert status, and the first change status.

16. The method of claim 15 further comprising:
applying a second pressure sensor to the target surface;
sensing by the second pressure sensor, at a second frequency a second pressure applied to the target surface;
calibrating, by the processor, the second pressure sensor to a second pressure range within which the second pressure sensor senses the second pressure;
providing second measurement parameters comprising a second threshold value corresponding to a second threshold pressure, a second measurement time period, a second alert value, and a second change condition;
comparing the second pressure to the second threshold pressure to provide a second comparative pressure;
integrating, by the processor, the second comparative pressure over the second time measurement period to provide a second integrated pressure;
comparing the second integrated pressure with the second alert value to determine a second alert status;
comparing the second integrated pressure with the second change condition to determine a second change status;
changing at least one measurement parameter or recalibrating the second pressure range to the second recalibrated pressure range, according to the second change status; and
displaying at least one of the second integrated pressure, the second alert status, and the second change status.

17. The method of claim 16 wherein displaying the first integrated pressure, the first alert status, the second integrated pressure, and the second alert status comprises visually displaying data of the first and second comparative pressures and the relative locations of the first and second pressure sensors on the target area.

18. The method of claim 15 further comprising:
applying a biological parameter sensor to the target surface;
sensing at a biological parameter frequency a biological parameter at the target surface;
providing measurement parameters comprising a biological parameter threshold value corresponding to a biological parameter threshold, a biological parameter measurement time period, a biological parameter alert value, and a biological parameter change condition;
comparing the biological parameter to the biological parameter threshold pressure to provide a comparative biological parameter value;
integrating, by the processor, the comparative biological parameter over the biological parameter time measurement period to provide an integrated biological parameter pressure;
comparing the integrated biological parameter with the biological parameter alert value to determine a biological parameter alert status;
comparing the integrated biological parameter with the biological parameter change condition to determine a biological parameter change status;

changing at least one measurement parameter or recalibrating the first pressure range to the first recalibrated pressure range, according to the biological parameter change status; and displaying, at the output device, at least one of the integrated biological parameter value, the biological parameter alert status, and the biological parameter change status.

* * * * *